(12) United States Patent
Chanduszko

(10) Patent No.: US 8,758,403 B2
(45) Date of Patent: *Jun. 24, 2014

(54) PFO CLOSURE DEVICE WITH FLEXIBLE THROMBOGENIC JOINT AND IMPROVED DISLODGEMENT RESISTANCE

(75) Inventor: Andrzej J. Chanduszko, Chandler, AZ (US)

(73) Assignee: W.L. Gore & Associates, Inc., Flagstaff, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/171,162

(22) Filed: Jun. 28, 2011

(65) Prior Publication Data

US 2012/0029560 A1 Feb. 2, 2012

Related U.S. Application Data

(63) Continuation of application No. 11/870,150, filed on Oct. 10, 2007, now Pat. No. 7,967,840, which is a continuation of application No. 10/662,000, filed on Sep. 12, 2003, now Pat. No. 7,318,833, which is a continuation-in-part of application No. 10/326,535, filed on Dec. 19, 2002, now Pat. No. 7,867,250.

(60) Provisional application No. 60/340,858, filed on Dec. 19, 2001.

(51) Int. Cl.
*A61F 2/06* (2013.01)

(52) U.S. Cl.
USPC .......... 606/215; 606/213; 606/155; 606/157; 606/153; 606/200; 604/500

(58) Field of Classification Search
USPC ......... 606/213, 215, 216, 153, 155, 157, 200; 604/500, 107
See application file for complete search history.

(56) References Cited

U.S. PATENT DOCUMENTS

| 3,294,631 A | 12/1966 | Loren et al. |
| 3,824,631 A | 7/1974 | Burstein et al. |
| 3,874,388 A | 4/1975 | King et al. |
| 3,875,648 A | 4/1975 | Bone |

(Continued)

FOREIGN PATENT DOCUMENTS

| DE | 9 413 645 | 10/1994 |
| EP | 0 362 113 | 4/1990 |

(Continued)

OTHER PUBLICATIONS

Athanasion T., "Coronary Artery Bypass with the Use of a Magnetic Distal Anastomotic Device: Surgical Technique and Preliminary Experience", *The Heart Surgery Forum* #2004-1024, 2004, 4 pgs.

(Continued)

*Primary Examiner* — Vy Q Bui
(74) *Attorney, Agent, or Firm* — DLA Piper LLP (US)

(57) ABSTRACT

The present invention provides devices for closing septal defects, such as a patent foramen ovale (PFO). The closure devices include a proximal anchor member, a distal anchor member, and at least one flexible center joint connecting the two anchor members. According to some embodiments, the proximal and/or distal anchor members may include a generally cylindrical member split along the central portion of its length to form an elongate oval. The proximal and/or distal anchor members may further include a tissue scaffold. At least some of the closure devices according to the present invention are repositionable and retrievable.

3 Claims, 25 Drawing Sheets

(56) References Cited

U.S. PATENT DOCUMENTS

| | | |
|---|---|---|
| 3,924,631 A | 12/1975 | Mancusi, Jr. |
| 4,006,747 A | 2/1977 | Kronenthal et al. |
| 4,007,743 A | 2/1977 | Blake |
| 4,149,327 A | 4/1979 | Hammer et al. |
| 4,235,238 A | 11/1980 | Ogiu et al. |
| 4,425,908 A | 1/1984 | Simon |
| 4,610,674 A | 9/1986 | Suzuki et al. |
| 4,626,245 A | 12/1986 | Weinstein |
| 4,696,300 A | 9/1987 | Anderson |
| 4,710,192 A | 12/1987 | Liotta et al. |
| 4,836,204 A | 6/1989 | Landymore et al. |
| 4,840,623 A | 6/1989 | Quackenbush |
| 4,852,568 A | 8/1989 | Kensey |
| 4,902,508 A | 2/1990 | Badylak et al. |
| 4,915,107 A | 4/1990 | Rebuffat et al. |
| 4,917,089 A | 4/1990 | Sideris |
| 4,956,178 A | 9/1990 | Badylak et al. |
| 5,021,059 A | 6/1991 | Kensey et al. |
| 5,037,433 A | 8/1991 | Wilk et al. |
| 5,041,129 A | 8/1991 | Hayhurst et al. |
| 5,078,736 A | 1/1992 | Behl |
| 5,106,913 A | 4/1992 | Yamaguchi et al. |
| 5,108,420 A | 4/1992 | Marks |
| 5,149,327 A | 9/1992 | Oshiyama |
| 5,167,363 A | 12/1992 | Adkinson et al. |
| 5,167,637 A | 12/1992 | Okada et al. |
| 5,171,259 A | 12/1992 | Inoue |
| 5,192,301 A | 3/1993 | Kamiya et al. |
| 5,222,974 A | 6/1993 | Kensey et al. |
| 5,226,879 A | 7/1993 | Ensminger et al. |
| 5,236,440 A | 8/1993 | Hlavacek |
| 5,245,023 A | 9/1993 | Peoples et al. |
| 5,245,080 A | 9/1993 | Aubard et al. |
| 5,250,430 A | 10/1993 | Peoples et al. |
| 5,257,637 A | 11/1993 | El Gazayerli |
| 5,269,809 A | 12/1993 | Hayhurst et al. |
| 5,275,826 A | 1/1994 | Badylak et al. |
| 5,282,827 A | 2/1994 | Kensey et al. |
| 5,284,488 A | 2/1994 | Sideris |
| 5,304,184 A | 4/1994 | Hathaway et al. |
| 5,312,341 A | 5/1994 | Turi |
| 5,312,435 A | 5/1994 | Nash et al. |
| 5,316,262 A | 5/1994 | Koebler |
| 5,334,217 A | 8/1994 | Das |
| 5,350,363 A | 9/1994 | Goode et al. |
| 5,350,399 A | 9/1994 | Erlebacher et al. |
| 5,354,308 A | 10/1994 | Simon et al. |
| 5,411,481 A | 5/1995 | Allen et al. |
| 5,411,520 A | 5/1995 | Nash et al. |
| 5,413,584 A | 5/1995 | Schulze |
| 5,417,699 A | 5/1995 | Klein et al. |
| 5,425,744 A | 6/1995 | Fagan et al. |
| 5,433,727 A | 7/1995 | Sideris |
| 5,451,235 A | 9/1995 | Lock et al. |
| 5,470,337 A | 11/1995 | Moss |
| 5,478,353 A | 12/1995 | Yoon |
| 5,480,353 A | 1/1996 | Garza, Jr. |
| 5,480,424 A | 1/1996 | Cox |
| 5,486,193 A | 1/1996 | Bourne et al. |
| 5,507,811 A | 4/1996 | Koike et al. |
| 5,534,432 A | 7/1996 | Peoples et al. |
| 5,540,712 A | 7/1996 | Kleshinski et al. |
| 5,549,617 A | 8/1996 | Green et al. |
| 5,562,632 A | 10/1996 | Davila et al. |
| 5,571,138 A | 11/1996 | Blomqvist et al. |
| 5,577,299 A | 11/1996 | Thompson et al. |
| 5,601,571 A | 2/1997 | Moss |
| 5,618,311 A | 4/1997 | Gryskiewicz |
| 5,618,314 A | 4/1997 | Harwin et al. |
| 5,620,461 A | 4/1997 | Muijs Van De Moer et al. |
| 5,626,599 A | 5/1997 | Bourne et al. |
| 5,634,936 A | 6/1997 | Linden et al. |
| 5,649,950 A | 7/1997 | Bourne et al. |
| 5,649,959 A | 7/1997 | Hannam et al. |
| 5,662,681 A | 9/1997 | Nash et al. |
| 5,663,063 A | 9/1997 | Peoples et al. |
| 5,683,411 A | 11/1997 | Kavteladze et al. |
| 5,690,674 A | 11/1997 | Diaz |
| 5,693,085 A | 12/1997 | Buirge et al. |
| 5,702,421 A | 12/1997 | Schneidt |
| 5,709,707 A | 1/1998 | Lock et al. |
| 5,717,259 A | 2/1998 | Schexnayder |
| 5,720,754 A | 2/1998 | Middleman et al. |
| 5,725,552 A | 3/1998 | Kotula et al. |
| 5,733,294 A | 3/1998 | Forber et al. |
| 5,733,337 A | 3/1998 | Carr, Jr. et al. |
| 5,741,297 A | 4/1998 | Simon |
| 5,776,162 A | 7/1998 | Kleshinski |
| 5,776,183 A | 7/1998 | Kanesaka et al. |
| 5,797,960 A | 8/1998 | Stevens et al. |
| 5,800,516 A | 9/1998 | Fine et al. |
| 5,810,884 A | 9/1998 | Kim |
| 5,823,956 A | 10/1998 | Roth et al. |
| 5,829,447 A | 11/1998 | Stevens et al. |
| 5,853,420 A | 12/1998 | Chevillon et al. |
| 5,853,422 A | 12/1998 | Huebsch et al. |
| 5,855,614 A | 1/1999 | Stevens et al. |
| 5,861,003 A | 1/1999 | Latson et al. |
| 5,865,791 A | 2/1999 | Whayne et al. |
| 5,879,366 A | 3/1999 | Shaw et al. |
| 5,893,856 A | 4/1999 | Jacob et al. |
| 5,902,319 A | 5/1999 | Daley |
| 5,904,703 A | 5/1999 | Gilson |
| 5,919,200 A | 7/1999 | Stambaugh et al. |
| 5,924,424 A | 7/1999 | Stevens et al. |
| 5,928,250 A | 7/1999 | Koike et al. |
| 5,944,738 A | 8/1999 | Amplatz et al. |
| 5,955,110 A | 9/1999 | Patel et al. |
| 5,976,174 A | 11/1999 | Ruiz |
| 5,989,268 A | 11/1999 | Pugsley, Jr. et al. |
| 5,993,475 A | 11/1999 | Lin et al. |
| 5,993,844 A | 11/1999 | Abraham et al. |
| 5,997,575 A | 12/1999 | Whitson et al. |
| 6,010,517 A | 1/2000 | Baccaro |
| 6,024,756 A | 2/2000 | Huebsch et al. |
| 6,030,007 A | 2/2000 | Bassily et al. |
| 6,045,551 A | 4/2000 | Bonutti |
| 6,056,760 A | 5/2000 | Koike et al. |
| 6,071,998 A | 6/2000 | Muller et al. |
| 6,077,291 A | 6/2000 | Das |
| 6,077,880 A | 6/2000 | Castillo et al. |
| 6,079,414 A | 6/2000 | Roth |
| 6,080,182 A | 6/2000 | Shaw et al. |
| 6,096,347 A | 8/2000 | Geddes et al. |
| 6,106,913 A | 8/2000 | Scardino et al. |
| 6,113,609 A | 9/2000 | Adams |
| 6,113,611 A | 9/2000 | Allen et al. |
| 6,117,159 A | 9/2000 | Huebsch et al. |
| 6,126,686 A | 10/2000 | Badylak et al. |
| 6,132,438 A | 10/2000 | Fleischman et al. |
| 6,143,037 A | 11/2000 | Goldstein et al. |
| 6,152,144 A | 11/2000 | Lesh et al. |
| 6,165,183 A | 12/2000 | Kuehn et al. |
| 6,165,204 A | 12/2000 | Levinson et al. |
| 6,171,329 B1 | 1/2001 | Shaw et al. |
| 6,174,322 B1 | 1/2001 | Schneidt |
| 6,174,330 B1 | 1/2001 | Stinson |
| 6,187,039 B1 | 2/2001 | Hiles et al. |
| 6,190,353 B1 | 2/2001 | Makower et al. |
| 6,206,895 B1 | 3/2001 | Levinson |
| 6,206,907 B1 | 3/2001 | Marino et al. |
| 6,214,029 B1 | 4/2001 | Thill et al. |
| 6,217,590 B1 | 4/2001 | Levinson |
| 6,221,092 B1 | 4/2001 | Koike et al. |
| 6,227,139 B1 | 5/2001 | Nguyen et al. |
| 6,228,097 B1 | 5/2001 | Levinson et al. |
| 6,231,561 B1 | 5/2001 | Frazier et al. |
| 6,245,080 B1 | 6/2001 | Levinson |
| 6,245,537 B1 | 6/2001 | Williams et al. |
| 6,261,309 B1 | 7/2001 | Urbanski |
| 6,265,333 B1 | 7/2001 | Dzenis et al. |
| 6,270,515 B1 | 8/2001 | Linden et al. |
| 6,277,138 B1 | 8/2001 | Levinson et al. |
| 6,277,139 B1 | 8/2001 | Levinson et al. |

(56) References Cited

U.S. PATENT DOCUMENTS

| | | |
|---|---|---|
| 6,287,317 B1 | 9/2001 | Makower et al. |
| 6,290,674 B1 | 9/2001 | Roue et al. |
| 6,306,150 B1 | 10/2001 | Levinson |
| 6,306,424 B1 | 10/2001 | Vyakarnam et al. |
| 6,312,446 B1 | 11/2001 | Huebsch et al. |
| 6,316,262 B1 | 11/2001 | Huisman et al. |
| 6,319,263 B1 | 11/2001 | Levinson |
| 6,322,548 B1 | 11/2001 | Payne et al. |
| 6,328,727 B1 | 12/2001 | Frazier et al. |
| 6,334,872 B1 | 1/2002 | Termin et al. |
| 6,342,064 B1 | 1/2002 | Koike et al. |
| 6,344,048 B1 | 2/2002 | Chin et al. |
| 6,344,049 B1 | 2/2002 | Levinson et al. |
| 6,346,074 B1 | 2/2002 | Roth |
| 6,348,041 B1 | 2/2002 | Klint |
| 6,352,552 B1 | 3/2002 | Levinson et al. |
| 6,355,052 B1 | 3/2002 | Neuss et al. |
| 6,356,782 B1 | 3/2002 | Sirimanne et al. |
| 6,364,853 B1 | 4/2002 | French et al. |
| 6,371,904 B1 | 4/2002 | Sirimanne et al. |
| 6,375,625 B1 | 4/2002 | French et al. |
| 6,375,671 B1 | 4/2002 | Kobayashi et al. |
| 6,379,342 B1 | 4/2002 | Levinson |
| 6,379,368 B1 | 4/2002 | Corcoran et al. |
| 6,387,104 B1 | 5/2002 | Pugsley, Jr. et al. |
| 6,398,796 B2 | 6/2002 | Levinson |
| 6,402,772 B1 | 6/2002 | Amplatz et al. |
| 6,406,420 B1 | 6/2002 | McCarthy et al. |
| 6,419,669 B1 | 7/2002 | Frazier et al. |
| 6,426,145 B1 | 7/2002 | Moroni |
| 6,436,088 B2 | 8/2002 | Frazier et al. |
| 6,440,152 B1 | 8/2002 | Gainor et al. |
| 6,460,749 B1 | 10/2002 | Levinson et al. |
| 6,482,224 B1 | 11/2002 | Michler et al. |
| 6,488,706 B1 | 12/2002 | Solymar |
| 6,494,888 B1 | 12/2002 | Laufer et al. |
| 6,508,828 B1 | 1/2003 | Akerfeldt et al. |
| 6,514,515 B1 | 2/2003 | Williams |
| 6,548,569 B1 | 4/2003 | Williams et al. |
| 6,551,303 B1 | 4/2003 | Van Tassel et al. |
| 6,551,344 B2 | 4/2003 | Thill |
| 6,585,755 B2 | 7/2003 | Jackson et al. |
| 6,596,013 B2 | 7/2003 | Yang et al. |
| 6,599,448 B1 | 7/2003 | Ehrhard, Jr. et al. |
| 6,610,764 B1 | 8/2003 | Martin et al. |
| 6,616,675 B1 | 9/2003 | Evard et al. |
| 6,623,508 B2 | 9/2003 | Shaw et al. |
| 6,623,518 B2 | 9/2003 | Thompson et al. |
| 6,626,936 B2 | 9/2003 | Stinson |
| 6,629,901 B2 | 10/2003 | Huang |
| 6,666,861 B1 | 12/2003 | Grabek |
| 6,669,722 B2 | 12/2003 | Chen et al. |
| 6,689,589 B2 | 2/2004 | Huisman et al. |
| 6,712,804 B2 | 3/2004 | Roue et al. |
| 6,712,836 B1 | 3/2004 | Berg et al. |
| 6,726,696 B1 | 4/2004 | Houser et al. |
| 6,786,915 B2 | 9/2004 | Akerfeldt et al. |
| 6,828,357 B1 | 12/2004 | Martin et al. |
| 6,838,493 B2 | 1/2005 | Williams et al. |
| 6,867,247 B2 | 3/2005 | Williams et al. |
| 6,867,248 B1 | 3/2005 | Martin et al. |
| 6,867,249 B2 | 3/2005 | Lee |
| 6,921,410 B2 | 7/2005 | Porter |
| 7,033,393 B2 | 4/2006 | Gainor et al. |
| 7,048,754 B2 | 5/2006 | Martin et al. |
| 7,087,072 B2 | 8/2006 | Marino et al. |
| 7,318,833 B2 | 1/2008 | Chanduszko |
| 7,361,180 B2 | 4/2008 | Saadat et al. |
| 7,416,554 B2 | 8/2008 | Lam et al. |
| 2001/0010481 A1 | 8/2001 | Blanc et al. |
| 2001/0014800 A1 | 8/2001 | Frazier et al. |
| 2001/0034537 A1 | 10/2001 | Shaw et al. |
| 2001/0034567 A1 | 10/2001 | Allen et al. |
| 2001/0037129 A1 | 11/2001 | Thill |
| 2001/0039435 A1 | 11/2001 | Roue et al. |
| 2001/0041914 A1 | 11/2001 | Frazier et al. |
| 2001/0041915 A1 | 11/2001 | Roue et al. |
| 2001/0044639 A1 | 11/2001 | Levinson |
| 2001/0049492 A1 | 12/2001 | Frazier et al. |
| 2002/0010481 A1 | 1/2002 | Jayaraman |
| 2002/0019648 A1 | 2/2002 | Akerfeldt et al. |
| 2002/0026208 A1 | 2/2002 | Roe et al. |
| 2002/0029048 A1 | 3/2002 | Miller |
| 2002/0032459 A1 | 3/2002 | Horzewski et al. |
| 2002/0032462 A1 | 3/2002 | Houser et al. |
| 2002/0034259 A1 | 3/2002 | Tada |
| 2002/0035374 A1 | 3/2002 | Borillo et al. |
| 2002/0043307 A1 | 4/2002 | Ishida et al. |
| 2002/0052572 A1 | 5/2002 | Franco et al. |
| 2002/0058989 A1 | 5/2002 | Chen et al. |
| 2002/0077555 A1 | 6/2002 | Schwartz |
| 2002/0095174 A1 | 7/2002 | Tsugita et al. |
| 2002/0096183 A1 | 7/2002 | Stevens et al. |
| 2002/0099389 A1 | 7/2002 | Michler et al. |
| 2002/0107531 A1 | 8/2002 | Schreck et al. |
| 2002/0111537 A1 | 8/2002 | Taylor et al. |
| 2002/0111637 A1 | 8/2002 | Kaplan et al. |
| 2002/0111647 A1 | 8/2002 | Khairkhahan et al. |
| 2002/0120323 A1 | 8/2002 | Thompson et al. |
| 2002/0128680 A1 | 9/2002 | Pavlovic |
| 2002/0129819 A1 | 9/2002 | Feldman et al. |
| 2002/0164729 A1 | 11/2002 | Skraly et al. |
| 2002/0169377 A1 | 11/2002 | Khairkhahan et al. |
| 2002/0183786 A1 | 12/2002 | Girton |
| 2002/0183787 A1 | 12/2002 | Wahr et al. |
| 2002/0183823 A1 | 12/2002 | Pappu |
| 2002/0198563 A1 | 12/2002 | Gainor et al. |
| 2003/0004533 A1 | 1/2003 | Dieck et al. |
| 2003/0023266 A1 | 1/2003 | Welch et al. |
| 2003/0028213 A1 | 2/2003 | Thill et al. |
| 2003/0045893 A1 | 3/2003 | Ginn |
| 2003/0050665 A1 | 3/2003 | Ginn |
| 2003/0055455 A1 | 3/2003 | Yang et al. |
| 2003/0057156 A1 | 3/2003 | Peterson et al. |
| 2003/0059640 A1 | 3/2003 | Marton et al. |
| 2003/0065379 A1 | 4/2003 | Babbs et al. |
| 2003/0100920 A1 | 5/2003 | Akin et al. |
| 2003/0120337 A1 | 6/2003 | Van Tassel et al. |
| 2003/0139819 A1 | 7/2003 | Beer et al. |
| 2003/0171774 A1 | 9/2003 | Freudenthal et al. |
| 2003/0191495 A1 | 10/2003 | Ryan et al. |
| 2003/0195530 A1 | 10/2003 | Thill |
| 2003/0204203 A1 | 10/2003 | Khairkhahan et al. |
| 2004/0044361 A1 | 3/2004 | Frazier et al. |
| 2004/0073242 A1 | 4/2004 | Chanduszko |
| 2004/0176799 A1 | 9/2004 | Chanduszko et al. |
| 2004/0210301 A1 | 10/2004 | Obermiller |
| 2004/0234567 A1 | 11/2004 | Dawson |
| 2005/0025809 A1 | 2/2005 | Hasirci et al. |
| 2005/0043759 A1 | 2/2005 | Chanduszko |
| 2005/0113868 A1 | 5/2005 | Devellian et al. |
| 2005/0267523 A1 | 12/2005 | Devellian et al. |
| 2005/0273124 A1 | 12/2005 | Chanduszko |
| 2005/0273135 A1 | 12/2005 | Chanduszko et al. |
| 2005/0288786 A1 | 12/2005 | Chanduszko |
| 2006/0122647 A1 | 6/2006 | Callaghan et al. |
| 2006/0217761 A1 | 9/2006 | Opolski |
| 2006/0265004 A1 | 11/2006 | Callaghan et al. |
| 2007/0010851 A1 | 1/2007 | Chanduszko et al. |
| 2007/0167981 A1 | 7/2007 | Opolski et al. |

FOREIGN PATENT DOCUMENTS

| | | |
|---|---|---|
| EP | 0 474 887 | 3/1992 |
| EP | 0 839 549 | 5/1998 |
| EP | 1 013 227 | 6/2000 |
| EP | 1 046 375 | 10/2000 |
| EP | 1 222 897 | 7/2002 |
| JP | 2002-355249 | 12/2002 |
| WO | WO 96/25179 A1 | 8/1996 |
| WO | WO 96/31157 A1 | 10/1996 |
| WO | WO 98/07375 A | 2/1998 |
| WO | WO 98/08462 A2 | 3/1998 |
| WO | WO 98/16174 A1 | 4/1998 |

(56) References Cited

FOREIGN PATENT DOCUMENTS

| WO | WO 98/18864 A1 | 5/1998 |
|----|----|----|
| WO | WO 98/29026 A2 | 7/1998 |
| WO | WO 98/51812 A2 | 11/1998 |
| WO | WO 99/05977 A1 | 2/1999 |
| WO | WO 99/18862 A1 | 4/1999 |
| WO | WO 99/18864 A1 | 4/1999 |
| WO | WO 99/18870 A1 | 4/1999 |
| WO | WO 99/18871 A1 | 4/1999 |
| WO | WO 99/30640 A1 | 6/1999 |
| WO | WO 00/27292 A1 | 5/2000 |
| WO | WO 00/44428 A1 | 8/2000 |
| WO | WO 01/21247 A1 | 3/2001 |
| WO | WO 01/30268 A1 | 5/2001 |
| WO | WO 01/49185 A1 | 7/2001 |
| WO | WO 01/78596 A1 | 10/2001 |
| WO | WO 02/17809 A1 | 3/2002 |
| WO | WO 02/24106 A2 | 3/2002 |
| WO | WO 03/024337 A1 | 3/2003 |
| WO | WO 03/053493 A2 | 7/2003 |
| WO | WO 03/059152 A2 | 7/2003 |
| WO | WO 03/063732 A2 | 8/2003 |
| WO | WO 03/077733 A2 | 9/2003 |
| WO | WO 03/082076 A2 | 10/2003 |
| WO | WO 03/103476 A2 | 12/2003 |
| WO | WO 2004/032993 A2 | 4/2004 |
| WO | WO 2004/037333 A1 | 5/2004 |
| WO | WO 2004/043266 A2 | 5/2004 |
| WO | WO 2004/043508 A1 | 5/2004 |
| WO | WO 2004/052213 A1 | 6/2004 |
| WO | WO 2005/006990 A2 | 1/2005 |
| WO | WO 2005/018728 A2 | 3/2005 |
| WO | WO 2005/027752 A1 | 3/2005 |
| WO | WO 2005/074813 A1 | 8/2005 |
| WO | WO 2005/092203 A1 | 10/2005 |
| WO | WO 2005/110240 A1 | 11/2005 |
| WO | WO 2005/112779 A1 | 12/2005 |
| WO | WO 2006/036837 A2 | 4/2006 |
| WO | WO 2006/102213 A1 | 9/2006 |

OTHER PUBLICATIONS

Bachthaler et al., "Corrosion of Tungsten Coils After Peripheral Vascular Embolization Theraphy: Influence on Outcome and Tungsten Load", *Catherization and Cardiovascular Interventions*, 62:380-384 (2004).

European Examination Report, European Application No. 04781644.2, mailed Aug. 23, 2007 (3 Pages).

Falk V., "Facilitated Endoscopic Beating Heart Coronary Artery Bypass Grafting Using a Magentic Coupling Device", *Journal of Thoracic and Cardiovascular Surgery*, 126,(5):1575-1579.

Filsoufi et al., "Automated Distal Coronary Bypass with a Novel Magnetic Coupler (MVP system)", *J. Thoracic and Cardiovascular Surgery*, 127(1):185-192.

International Search Report for International Patent Application No. PCT/AU03/00759, filed Jun. 19, 2003.

International Search Report, International Application No. PCT/US03/17390, mailed on Oct. 6, 2003, 4 pgs.

International Search Report, International Application No. PCT/US02/40850 mailed Jun. 19, 2003 (4 pgs).

International Search Report, International Application No. PCT/US03/01050, mailed Jul. 8, 2003 (1 pg).

International Search Report, International Application No. PCT/US03/09051, mailed Sep. 29, 2003 (2 pgs).

International Search Report, International Application No. PCT/US03/17715, mailed Mar. 24, 2004 (2 pgs).

International Search Report, International Application No. PCT/US03/32133, mailed Apr. 22, 2004 (1 pg).

International Search Report, International Application No. PCT/US03/34003 mailed Oct. 3, 2004 (4 pgs).

International Search Report, International Application No. PCT/US03/35479, mailed Apr. 14, 2004 (2 pgs).

International Search Report, International Application No. PCT/US03/35998 mailed Jun. 16, 2004 (5 pgs).

International Search Report, International Application No. PCT/US03/39253, mailed Apr. 19, 2004 (4 pgs).

International Search Report, International Application No. PCT/US04/022643, mailed Mar. 31, 2005 (2 pgs).

International Search Report, International Application No. PCT/US04/026998, mailed Apr. 22, 2005 (5 pgs).

International Search Report, International Application No. PCT/US04/029978, mailed Jan. 26, 2005 (3 pgs).

International Search Report, International Application No. PCT/US05/006703, mailed Jul. 25, 2005 (3 pgs).

International Search Report, International Application No. PCT/US05/013705 mailed Aug. 4, 2005 (4 pgs).

International Search Report, International Application No. PCT/US05/015382, mailed Oct. 6, 2005 (4 pgs).

International Search Report, International Application No. PCT/US05/34276, mailed Oct. 9, 2007.

International Search Report, International Application No. PCT/US06/009978, mailed Jul. 13, 2006 (2 pgs).

International Search Report, International Application No. PCT/US2007/065526, mailed Aug. 8, 2007 (5 pgs).

International Search Report, International Application No. PCT/US2007/065541, mailed Aug. 7, 2007 (3 pgs).

International Search Report, International Application No. PCT/US97/14822, mailed Feb. 20, 1998 (2 pgs).

International Search Report, International Application No. PCT/US97/17927, mailed Feb. 10, 1998 (1 pg).

Isotalo et al., "Biocompatibility Testing of a New Bioabsorbable X-Ray Positive SR-PLA 96/4 Urethral Stent", *The Journal of Urology*, 163:1764-1767 (1999).

Kimura et al., "Effects of Neutron Irradiation on the Transformation Behavior in Ti-Ni Alloys", Abstract, *Proceedings of the Int'l Conf. on Mariensitic Transformations*, (1992) pp. 935-940.

Klima U., "Magnetic Vascular Port in Minimally Invasive Direct Coronary Artery Bypass Grafting", *Circulation*, 2004, II-55-II-60.

Meier and Lock, "Contemporary Management of Patent Foramen Ovale", American Heart Association, Inc., *Circulation*, 2003, vol. 107, pp. 5-9.

*Nat'l Aeronautics and Space Administration*, "55-Nitinol—The Alloy with a Memory: Its Physical Metallurgy, Properties, and Applications", A Report, pp. 24-25.

Parviainen et al., "A New Biodegradable Stent for the Pancreaticojejunal Anastomosis After Pancreaticoduodenal Resection: In Vitro Examination and Pilot Experiences in Humans", Pancreas, vol. 21, No. 1, pp. 14-21, 2000.

Ramanathan et al., "Experimental and Computational Methods for Shape Memory Alloys", $15.sup.th$ *ASCE Engineering Mechanics Conf.*, Jun. 2-5, 2003.

Ruddy et al., "Rheological, Mechanical and Thermal Behaviour of Radipaque Filled Polymers", *Polymer Processing Research Centre, School of Chemical Engineering, Queen's University of Belfast*, 5 pages.

Ruis et al., "The Puncture Technique: A New Method for Transcatheter Closure of Patent Foramen Ovale", *Catherterization and Cardiovascular Interventions*, 53, Wiley-Liss, Inc., 2001, pp. 369-372.

Shabalovskaya S., "Surface, corrosion and biocompatibility aspects of Nitinol as an implant material", *Bio-Medical materials and Engineering*, (2002) vol. 12, pp. 69-109.

SMST-2000, "Proceedings of the International Conference on Shape Memory and Superelastic Technologies", Apr. 30 to May 4, 2000, *Asilomar Conference Center*.

Stockel D., "Nitinol Medical Devices and Implants", *SMST—2000 Conference Proceedings*, 2001, pp. 531-541.

Uchil J., "Shape Memory Alloys—Characterization Techniques", Pramana—Journal of Physics, (2002) vol. 58, Nos. 5 & 6, pp. 1131-1139.

Vaajanen et al., "Expansion and Fixation Properties of a New Braided Biodegradable Urethral Stent: An Experimental Study in the Rabbit", *The Journal of Urology*, vol. 169, pp. 1771-1174, Mar. 2003.

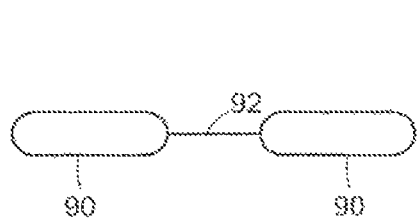
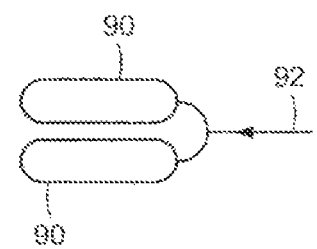
FIG. 11A    FIG. 11B
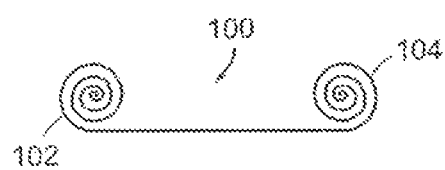
FIG. 12
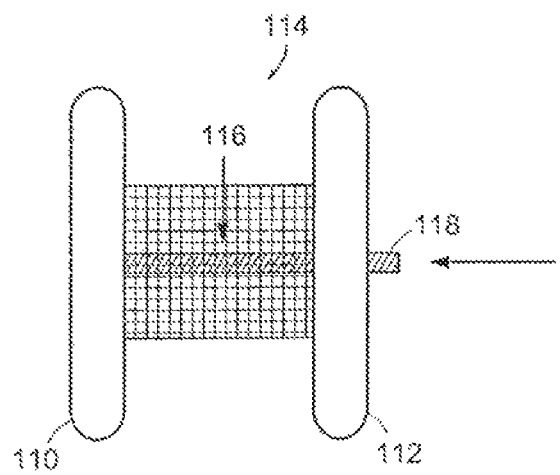
FIG. 13

PFO CLOSURE DEVICE WITH FLEXIBLE THROMBOGENIC JOINT AND IMPROVED DISLODGEMENT RESISTANCE

CROSS REFERENCE TO RELATED APPLICATIONS

This application is a continuation application of U.S. application Ser. No. 11/870,150 filed Oct. 10, 2007, now issued as U.S. Pat. No. 7,967,840; which is a continuation application of U.S. application Ser. No. 10/662,000 filed Sep. 12, 2003, now issued as U.S. Pat. No. 7,318,833; which is a continuation-in-part application of U.S. application Ser. No. 10/326,535 filed Dec. 19, 2002, now issued as U.S. Pat. No. 7,867,250; which claims the benefit under 35 USC §119(e) to U.S. Application Ser. No. 60/340,858 filed Dec. 19, 2001, now expired. The disclosure of each of the prior applications is considered part of and is incorporated by reference in the disclosure of this application.

BACKGROUND OF THE INVENTION

1. Field of the Invention

The present invention relates generally to an occlusion device for the closure of physical anomalies, such as a patent foramen ovale.

2. Background Information

A patent foramen ovale (PFO), illustrated in FIG. 1, is a persistent, one-way, usually flap-like opening in the wall between the right atrium 10 and left atrium 12 of the heart. Because left atrial (LA) pressure is normally higher than right atrial (RA) pressure, the flap usually stays closed. Under certain conditions, however, right atrial pressure can exceed left atrial pressure, creating the possibility that blood could pass from the right atrium 10 to the left atrium 12 and blood clots could enter the systemic circulation. It is desirable that this circumstance be eliminated.

The foramen ovale serves a desired purpose when a fetus is gestating in utero. Because blood is oxygenated through the umbilical chord, and not through the developing lungs, the circulatory system of the fetal heart allows the blood to flow through the foramen ovale as a physiologic conduit for right-to-left shunting. After birth, with the establishment of pulmonary circulation, the increased left atrial blood flow and pressure results in functional closure of the foramen ovale. This functional closure is subsequently followed by anatomical closure of the two over-lapping layers of tissue: septum primum 14 and septum secundum 16. However, a PFO has been shown to persist in a number of adults.

The presence of a PFO is generally considered to have no therapeutic consequence in otherwise healthy adults. Paradoxical embolism via a PFO is considered in the diagnosis for patients who have suffered a stroke or transient ischemic attack (TLA) in the presence of a PFO and without another identified cause of ischemic stroke. While there is currently no definitive proof of a cause-effect relationship, many studies have confirmed a strong association between the presence of a PFO and the risk for paradoxical embolism or stroke. In addition, there is significant evidence that patients with a PFO who have had a cerebral vascular event are at increased risk for future, recurrent cerebrovascular events.

Accordingly, patients at such an increased risk are considered for prophylactic medical therapy to reduce the risk of a recurrent embolic event. These patients are commonly treated with oral anticoagulants, which potentially have adverse side effects, such as hemorrhaging, hematoma, and interactions with a variety of other drugs. The use of these drugs can alter a person's recovery and necessitate adjustments in a person's daily living pattern.

In certain cases, such as when anticoagulation is contraindicated, surgery may be necessary or desirable to close a PFO. The surgery would typically include suturing a PFO closed by attaching septum secundum to septum primum. This sutured attachment can be accomplished using either an interrupted or a continuous stitch and is a common way a surgeon shuts a PFO under direct visualization.

Umbrella devices and a variety of other similar mechanical closure devices, developed initially for percutaneous closure of atrial septal defects (ASDs), have been used in some instances to close PFOs. These devices potentially allow patients to avoid the side effects often associated with anticoagulation therapies and the risks of invasive surgery. However, umbrella devices and the like that are designed for ASDs are not optimally suited for use as PFO closure devices.

Currently available septal closure devices present drawbacks, including technically complex implantation procedures. Additionally, there are not insignificant complications due to thrombus, fractures of the components, conduction system disturbances, perforations of heart tissue, and residual leaks. Many devices have high septal profile and include large masses of foreign material, which may lead to unfavorable body adaptation of a device. Given that ASD devices are designed to occlude holes, many lack anatomic conformability to the flap-like anatomy of PFOs. Thus, when inserting an ASD device to close a PFO, the narrow opening and the thin flap may form impediments to proper deployment. Even if an occlusive seal is formed, the device may be deployed in the heart on an angle, leaving some components insecurely seated against the septum and, thereby, risking thrombus formation due to hemodynamic disturbances. Finally, some septal closure devices are complex to manufacture, which may result in inconsistent product performance.

The present invention is designed to address these and other deficiencies of prior art septal closure devices.

SUMMARY OF THE INVENTION

Various embodiments of the present invention are directed to devices for closing septal defects such as PFOs. The closure devices generally include a proximal anchor member, a distal anchor member, and a flexible center joint connecting the two anchor members. The center joint may be one or more sutures. Alternatively, the center joint may be a flexible elastomeric layer, which may promote tissue ingrowth or deliver drugs. The flexible material may also be covered with a biocompatible material to promote adherence to tissue or with growth factors to accelerate tissue ingrowth.

In accordance with some embodiments of the invention, the closure device is formed of bioresorbable components such that substantially no permanent foreign material remains in the body.

In accordance with other embodiments of the invention, the proximal and/or distal anchor members of the closure device may include a generally cylindrical member split along the center portion of its length to form an elongate oval when the ends of the member are pressed together. Of course, a variety of cross section shapes in addition to a circular cross section may be used. Such proximal and/or distal anchor members may be two-dimensional or three-dimensional. Such proximal and/or distal anchor members may further include a tissue scaffold.

In accordance with further embodiments of the invention, mechanisms are provided to collapse the closure device in order to facilitate device delivery, removal and/or repositioning.

These and other features will become readily apparent from the following detailed description wherein embodiments of the invention are shown and described by way of illustration. As will be realized, the invention is capable of other and different embodiments and its several details may be capable of modifications in various respects, all without departing from the invention. Accordingly, the drawings and description are to be regarded as illustrative in nature and not in a restrictive or limiting sense.

BRIEF DESCRIPTION OF THE DRAWINGS

FIGS. 11A and 11B illustrate an anchor member with an elastic hinge in accordance with one or more further embodiments of the invention.

FIG. 12 illustrates a PFO closure device made from a single material in accordance with one or more further embodiments of the invention.

FIG. 13 illustrates a PFO closure device having inflatable anchor members in accordance with one or more further embodiments of the invention.

DETAILED DESCRIPTION OF THE INVENTION

Various embodiments of the present invention are directed to methods and devices for closing septal defects such as PFOs, primarily by eliciting a healing response at the defect. The device may have various configurations that, in general, include an anchor member on each side of the septal defect with at least one connecting member between the anchor members that joins the anchor members. The at least one connecting member may have one of several configurations that promotes a healing response in the defect.

Figure 1:
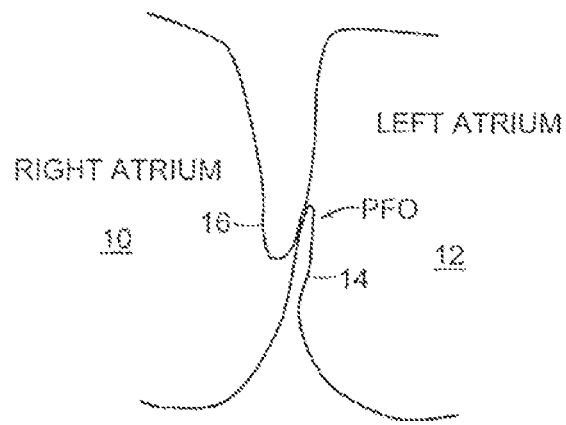
FIG. 1 is a cross-sectional view of a portion of the heart illustrating a PFO.
Figure 2:
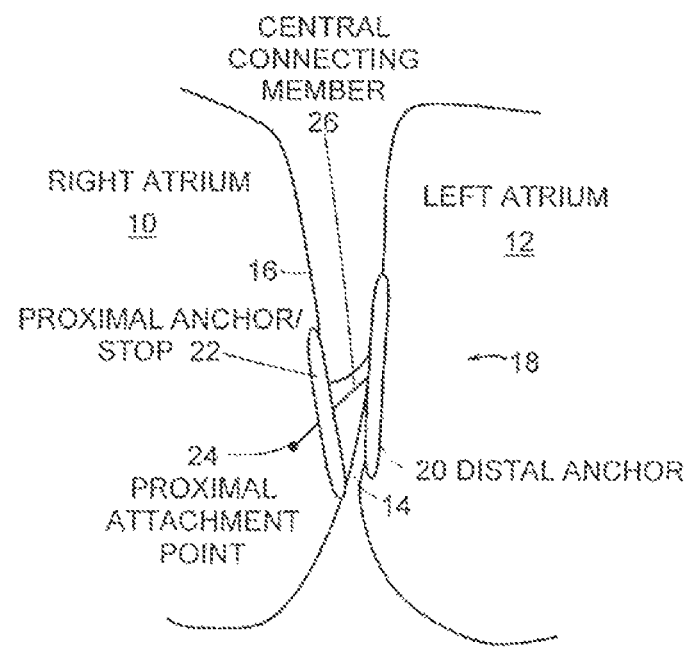
FIG. 2 illustrates a deployed PFO closure device with bioresorbable components in accordance with one or more embodiments of the invention.

As shown in FIG. 2, a PFO closure device 18 in accordance with one or more embodiments of the present invention includes a distal anchor component or member 20 (which can be placed on the left atrial side of the PFO), a proximal anchor member 22 (to fix the device in place), a proximal attachment point 24 (for attachment and release from a catheter), and a central connecting member 26 (which can, for example, be a simple suture in accordance with this embodiment).

In some embodiments, the distal anchor, the proximal anchor, and the connecting member are bioresorbable. These components can be fabricated from either a single bioresorbable polymer or by a laminated composite of two or more materials to provide a unique mix of properties such as, for example, anchor members having stiff centers and flexible edges, and blood contacting surfaces having controlled porosity or surface texture to promote fast and thorough endothelialization, while minimizing thrombosis. In addition, the tissue-contacting surface of the anchors can be designed to provide added stability by, for example, being roughened.

The distal anchor 20 is an elongated, preferably generally cylindrical, thin bar-like member with rounded, arcuately shaped ends. The tissue contacting surface of the anchor can be generally flattened to increase tissue surface contact. In size, the distal anchor component might, for example, be 15-30 mm long and 2 mm in diameter with a circular cross-section. The proximal anchor 22 can be of similar dimensions and shape, although it can be shorter in overall length.

Other distal and proximal anchor structures are also possible. For example, the anchors can be formed of a generally flat material rolled to form a cylindrical shape as described below with respect to the embodiments of FIGS. 20 and 21.

Figure 3:
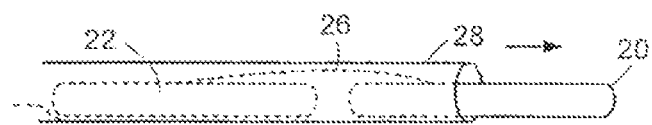
FIG. 3 illustrates the PFO closure device of FIG. 2 in a collapsed state for passage through a delivery catheter or sheath.

For delivery and deployment, the distal anchor 20 and proximal anchor 22 are positioned to be generally aligned in a longitudinal, end-to-end manner within a delivery sheath or catheter 28 as shown in FIG. 3. These components, with the flexible connecting member 26, traverse the catheter or delivery sheath in this longitudinal orientation. The catheter or delivery sheath is inserted between septum primum and septum secundum into the left atrium 18, and the distal anchor component 20 is ejected. Then, the catheter or delivery sheath 28 is withdrawn into the right atrium, and the proximal anchor 22 is ejected. The flexible central connecting member 26 extends between septum primum and septum secundum to join the distal anchor 20 and the proximal anchor 22. Once ejected, the distal anchor and proximal anchor generally self-orientate to be essentially perpendicular to the axis of the central connecting member and in generally parallel planes to one another. The exact orientation will be governed by the individual patient's anatomy. The terms "withdrawn" and "ejected" are relative and are intended to generically describe the relative movement of the device with respect to the delivery catheter.

An alternate delivery method for this device can be to deploy it directly through the septum primum as opposed to through the PFO.

The method of attaching the central connecting member 26 to the anchor and stop mechanism 22 to permit the distal anchor and the proximal anchor to be drawn together could be, for example, via a friction fit or via a slip knot on the central connecting member. If a slip knot is used, the free end of the suture proximal to the knot can be held remotely and released after the knot has been placed in the appropriate location.

Figure 4:
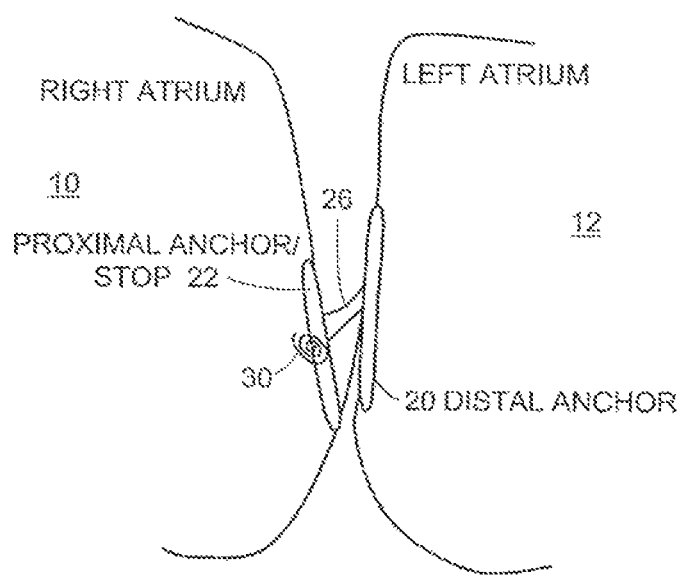
FIG. 4 illustrates a closure device deployed to close a PFO in accordance with one or more further embodiments of the invention.

In one or more alternate embodiments of the invention shown in FIG. 4, the central connecting member 26 is mounted to permit free sliding movement of the proximal anchor 22 relative to the central connecting member 26. A biasing spring 30, which may be an expandable coil spring, can be formed at the outer end of the central connecting member 26 to bias the proximal anchor toward the distal anchor when both are deployed from the catheter or sheath.

Figure 5:
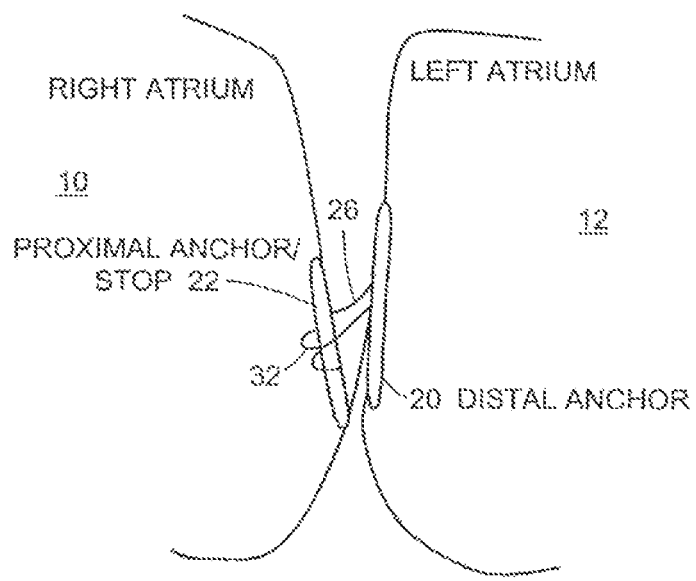
FIG. 5 illustrates a closure device deployed to close the PFO in accordance with one or more further embodiments of the invention.

In the embodiments illustrated in FIGS. 4 and 5, a metallic component may be used as the central connecting member 26 in order to provide an appropriate stop and apply compression force to the proximal anchor 22. The metallic component could be a piece of shape memory wire that has one end molded or laminated into the distal anchor component 20. In FIG. 4, the proximal anchor 22 slides on the central connecting member 26, and once it is deployed, the biasing spring 30 formed on the end of the shape memory wire expands to bias the proximal anchor 22 toward the distal anchor 20.

In the FIG. 5 embodiment, a shape memory wire forms a hook type anchor 32 made from two wires that exit through the center of the proximate anchor and curve in opposite directions when expanded to draw the proximate anchor toward the distal anchor.

While the embodiments of FIGS. 4 and 5 can leave a permanent foreign body when the bioresorbable components dissolve (if, for example, a metallic component is used as the central connecting member 26), one advantage of these devices is that no thrombogenic tissue scaffold (usually a vascular material) is placed on the left atrial side. Thrombus forming on the LA side of a PFO closure device can be released into the systemic circulation causing an embolic event within the coronary arteries, cerebral circulation, or distally in the vasculature, and most vascular graft materials utilized to close PFOs are highly thrombogenic.

The PFO closure devices may need to be capable of x-ray visualization and use with radiopaque fillers or marker bands, which may be fabricated from noble metals such as platinum or gold. These markers can be attached using a variety of common methods such as, for example, adhesive bonding, lamination between two layers of polymer, or vapor deposition.

Figure 6A:
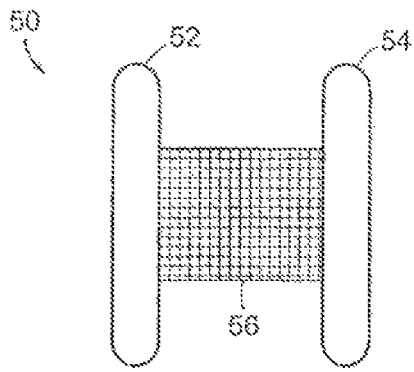
FIGS. 6A and 6B are front and side views, respectively, of a PFO closure device in accordance with one or more further embodiments of the invention.
Figure 6B:
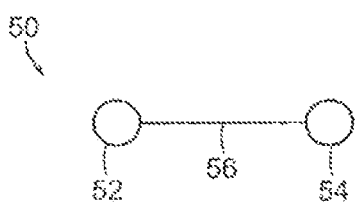

FIGS. 6A and 6B illustrate a closure device 50 in accordance with one or more further embodiments of the invention. The device 50 includes proximal and distal anchor members 52, 54 connected with a flexible (and preferably stretchable elastomeric) center joint or connecting element 56. The anchor members 52, 54 are preferably cylindrical in shape with rounded ends. In size, the distal anchor member 54 might, for example, be about 15-30 mm long and about 2 mm in diameter with a circular cross-section. The proximal anchor 52 can be of similar dimensions and shape, although it can be shorter in overall length. The anchor members 52, 54 are preferably made from a relatively rigid (preferably bioresorbable) polymer (regular or shape memory), or biological tissue. Biocompatible metal can also be used.

Other distal and proximal anchor structures are also possible. For example, the anchors can be formed of a generally flat material rolled to form a cylindrical shape as described below with respect to the embodiments of FIGS. 20 and 21.

Figure 7A:
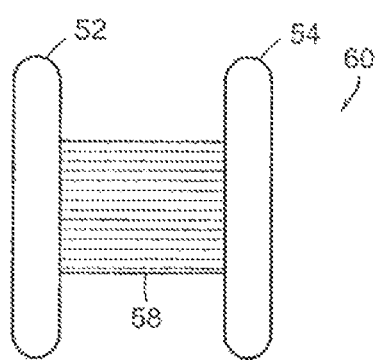
FIGS. 7A and 7B are front and side views, respectively, of a PFO closure device in accordance with one or more further embodiments of the invention.
Figure 7B:
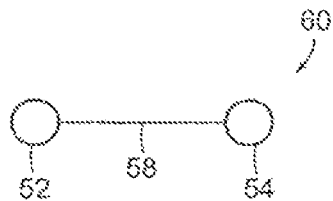

The center joint 56 of the FIG. 6 device (as well as the center joints of the devices shown in FIGS. 7 to 10, 12 to 18, and 21 to 24) are preferably elastomeric and resilient and are made from thrombogenic or inflammatory materials including, for example, polyester, biological tissue, bioresorbable polymer, small diameter springs (e.g., Nitinol springs), or spongy polymeric material. Alternatively, the center joint can be made of multiple strands of material 58 such as, for example, polymer fibers as shown in the closure device 60 of FIGS. 7A and 7B. The center joint can be textured, porous or in a form of a single or double-sided hook material such as Velcro. These kinds of surfaces produce inflammatory responses and therefore, promote faster tissue ingrowth and faster defect closure. The entire device or parts of it can be made from bioresorbable polymers.

Figure 8A:
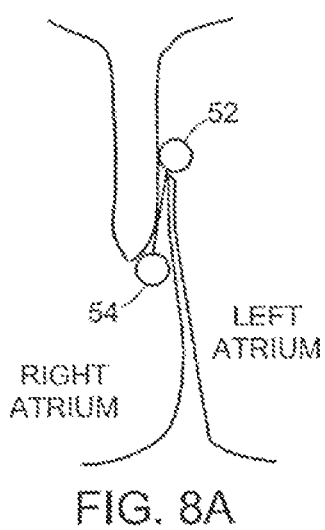
FIGS. 8A and 8B are side and front views, respectively, of the PFO closure device of FIG. 6 deployed to close a PFO.
Figure 8B:
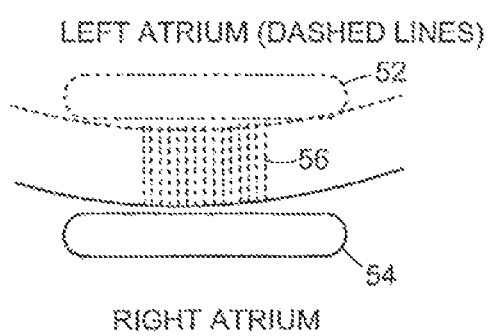

FIGS. 8A and 8B are front and side views, respectively, of the device 50 in a PFO defect. The proximal and distal anchor members 54, 52 are longer than the defect width, thereby inhibiting the device from being embolized.

Figure 9A:
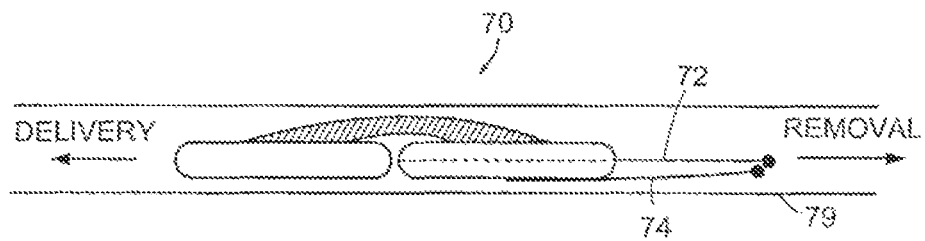
FIG. 9A illustrates a closure device having a retrieval mechanism in accordance with one or more further embodiments of the invention in a collapsed state for passage through a catheter or sheath.
Figure 9B:
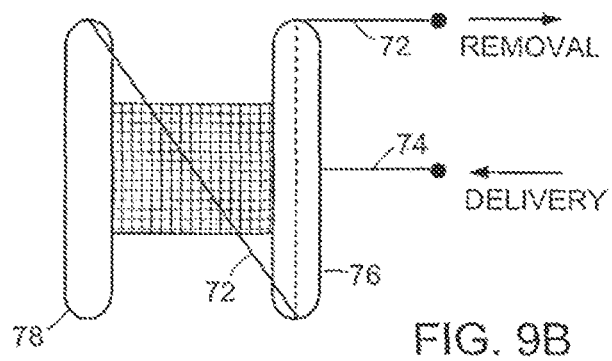
FIG. 9B is a front view of the FIG. 9A device.

In accordance with further embodiments of the invention, a closure device can include a delivery/removal mechanism to facilitate device delivery, removal or repositioning. A device 70 shown in FIGS. 9A and 9B includes a removal string 72 and a delivery string 74. The removal string is movably secured and slides freely inside of the proximal anchor member 76. The string extends from one end of the proximal member 76 and is fixed to an opposite end of the distal anchor member 78. By pulling on the free end of the removal string 72, the whole device 70 can be collapsed and pulled into the delivery sheath 79 as shown in FIG. 9A. The strings can, for example, be sutures or wires such as Nitinol wire.

Figure 9C:
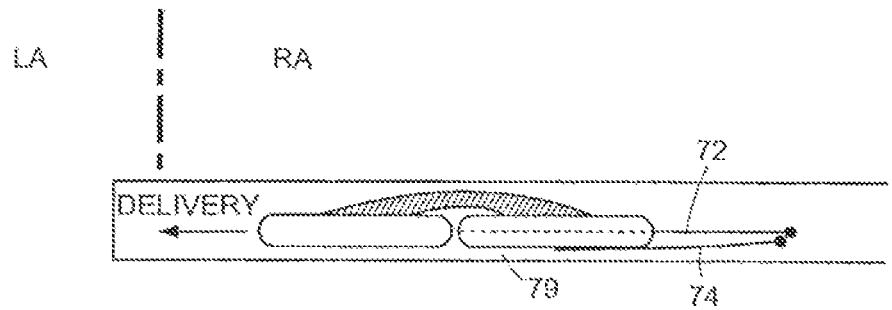
FIGS. 9C to 9E illustrate deployment of the FIG. 9A device.
Figure 9D:
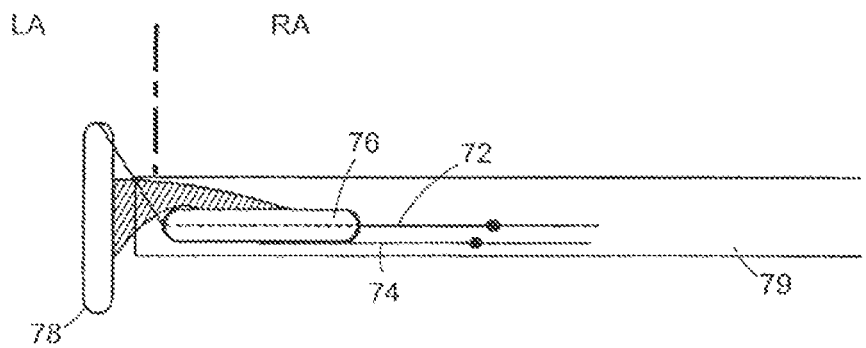
Figure 9E:
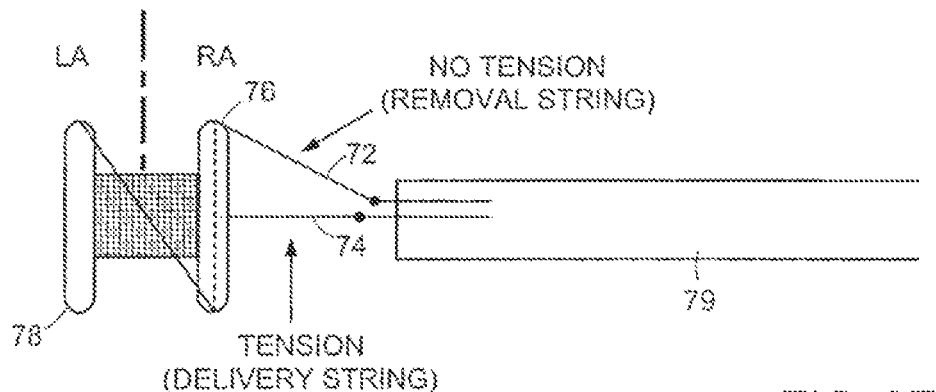

The delivery and removal strings are manipulated separately in order to deploy or remove the device. FIGS. 9C through 9E illustrate device deployment using the delivery string 74, which is preferably attached generally to the center of the proximal anchor member 76. The delivery sheath 79 containing the device 70 is first inserted between the septum primum and septum secundum into the left atrium as shown in FIG. 9C. As shown in FIG. 9D, the distal anchor 78 is then ejected from the delivery catheter 79. Tension is then applied to the delivery string 74, and the delivery sheath is withdrawn into the right atrium and the proximal anchor 76 is ejected. Applying tension to the delivery string enables the proximal anchor 76 to be properly deployed in the right atrium, and keeps the anchor 76 from being ejected into the left atrium. Upon successful deployment of the device 70, both strings are released and the delivery system is withdrawn. No tension is applied to the removal string during delivery.

Figure 9F:
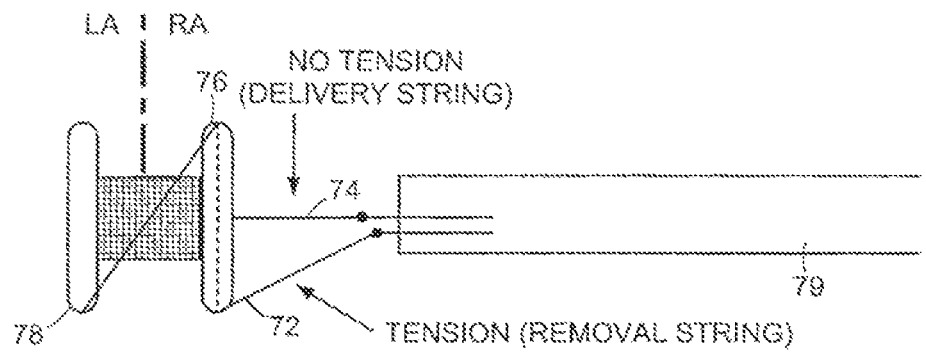
FIGS. 9F to 9H illustrate removal of the FIG. 9A device.
Figure 9G:
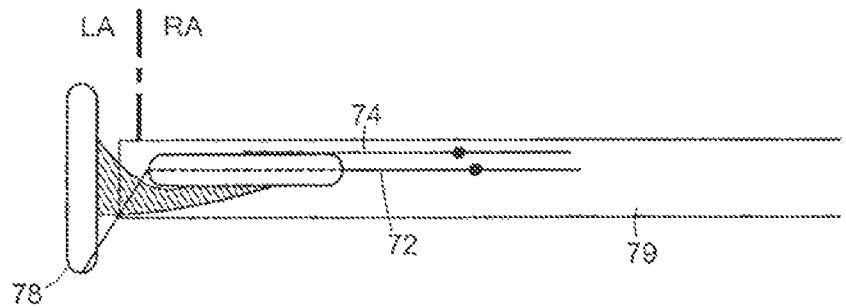
Figure 9H:
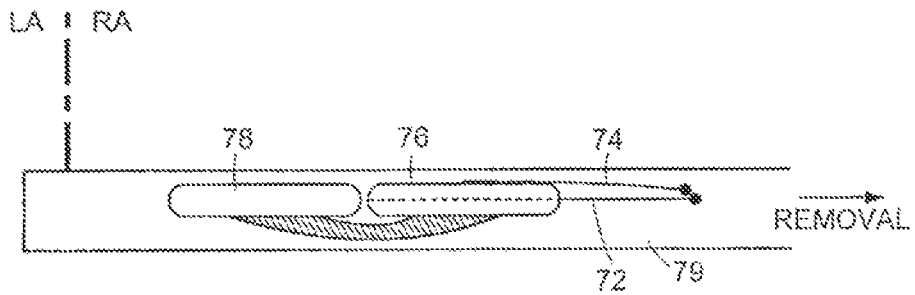

FIGS. 9F to 9H illustrate removal of the device 70. As shown in FIG. 9F, tension is applied to the removal string, while the delivery sheath 79 is moved toward the device 70. The applied tension causes the proximal anchor 76 to be withdrawn into the delivery sheath as shown in FIG. 9G. The distal anchor 78 is also withdrawn into the delivery sheath as further tension is applied to the removal string. The device can then be redeployed if desired or removed.

Alternatively, the delivery string 74 can be omitted, and the removal string 72 can be used for both device deployment and removal. The delivery sheath 79 containing the closure device is first inserted between septum primum and septum secundum into the left atrium in a similar manner to that shown in FIG. 9C. The distal anchor 78 is then ejected from the delivery catheter 79 in a similar manner to that shown in FIG. 9D. Tension is applied to the removal string 72, and the delivery sheath is withdrawn into the right atrium, and the proximal anchor 76 is ejected. Applying tension to the removal string enables the proximal anchor 76 to be properly deployed in the right atrium and keeps the proximal anchor 76 from being ejected into the left atrium. The elasticity of the center joint connecting the anchor members helps properly position the proximal anchor at the defect. Upon successful deployment of the closure device, the string 72 is released and the delivery system is withdrawn.

Figure 10A:
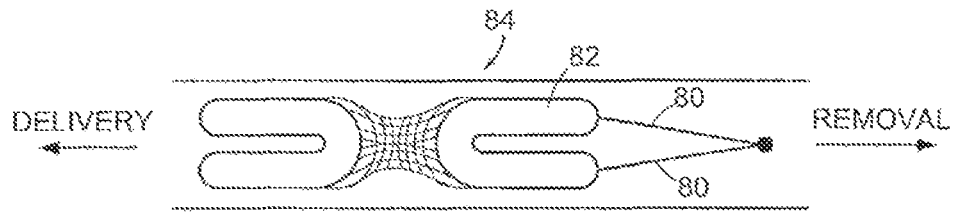
FIG. 10A illustrates a closure device having a retrieval mechanism in accordance with one or more further embodiments of the invention in a collapsed state for passage through a catheter or sheath.
Figure 10B:
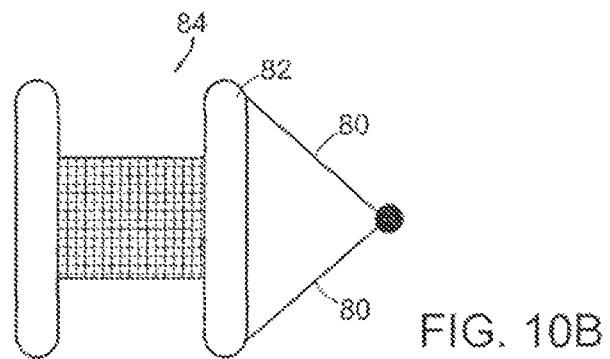
FIG. 10B is a front view of the FIG. 10A device.

As shown in FIGS. 10A and 10B, in another embodiment, strings 80 (suture, Nitinol wire, etc.) are attached to both ends of the proximal anchor member 82 of a closure device 84. Both anchor members are flexible and can fold as shown in FIG. 10A in order to be delivered to or removed from the defect.

In accordance with a further embodiment of the invention, as shown in FIGS. 11A and 11B, each of the proximal and distal anchor members can include two elements 90 separated by an elastic hinge 92. The elastic hinge 92 can facilitate folding of the members as shown in FIG. 11B. The hinge 92 can be molded or made from a material such as, for example, Nitinol or other shape memory materials, which can be a different material from the elements 90.

In accordance with some embodiments of the invention, an entire closure device can be made from a single sheet of a material as shown, for example, in the closure device 100 of FIG. 12. Two opposite ends of the sheet can be rolled to form the proximal and distal anchor members. Glue or heat bonding can be used to maintain the rolled-up configuration of the anchor members 102, 104.

As shown in FIG. 13, in accordance with some further embodiments of the invention, one or both anchor members 110, 112 of a closure device 114 can be inflatable. The anchor members can be inflated with, for example, saline or other physiological fluid during or before the delivery of the device. A tube 116 can communicate with cavities in the anchor members. An inlet 118 can be provided at one of the members for introducing fluid therein.

Figure 14:
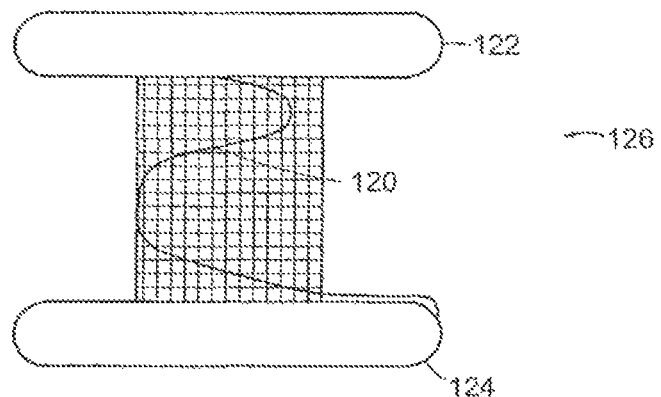
FIG. 14 illustrates a PFO closure device with a wire connecting the proximal and distal anchor members in accordance with one or more further embodiments of the invention.

In accordance with some further embodiments of the invention, a wire 120 such as, for example, an S-shaped wire, can be provided to connect the proximal and distal anchor members 122, 124 of a device 126 as shown in FIG. 14. The wire can be used to provide additional clamping force while the device is in a PFO defect. Other wire shapes are also possible.

Figure 15:
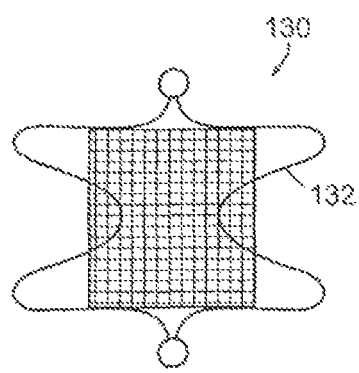
FIG. 15 illustrates a PFO closure device having a frame member in accordance with one or more further embodiments of the invention.
Figure 16:
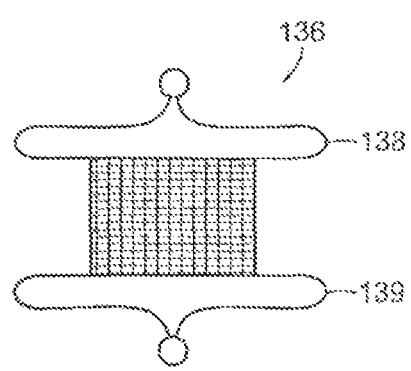
FIG. 16 illustrates a PFO closure device having frame anchor members in accordance with one or more further embodiments of the invention.

In accordance with further embodiments of the invention, one or more frame structures can be used as the anchor members of a closure device. For example, FIG. 15 shows a closure device 130 having a frame structure 132. Also, FIG. 16 shows a closure device 136 having frames 138, 139. The frames can be, for example, a metal (e.g., Nitinol wire) or polymer frame.

Figure 17:
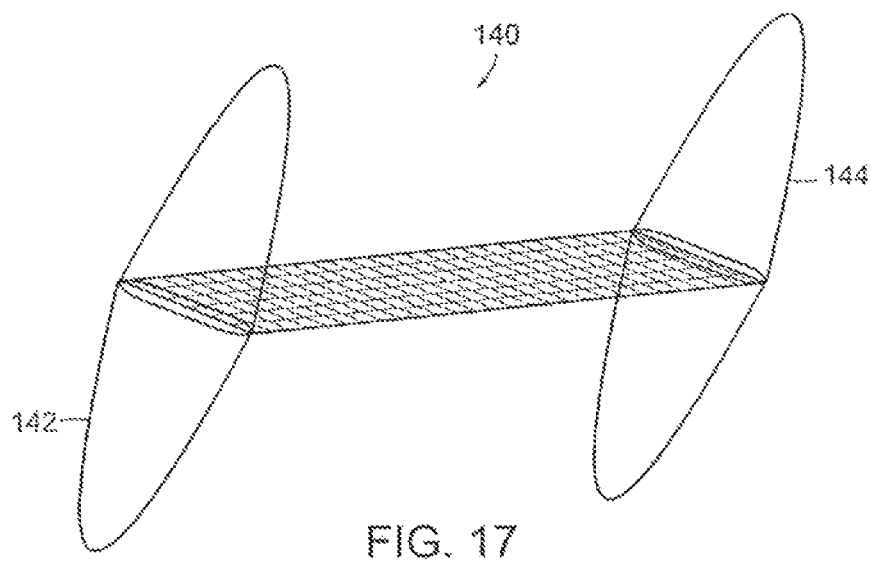
FIG. 17 illustrates a PFO closure device having frame anchor members in accordance with one or more further embodiments of the invention.
Figure 18:
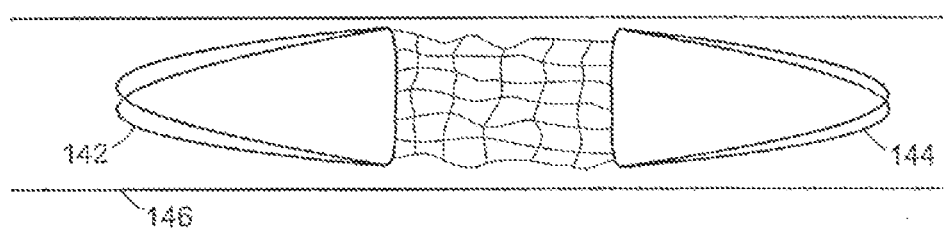
FIG. 18 illustrates the FIG. 17 device in a collapsed state for passage through a catheter or sheath.
Figure 19:
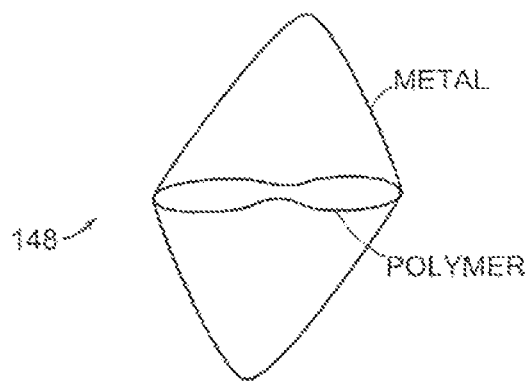
FIG. 19 illustrates a frame anchor member having metal and polymer components in accordance with one or more further embodiments of the invention.

FIGS. 17 to 19 illustrate closure devices in accordance with some further embodiments of the invention. A closure device 140 shown in FIG. 17 includes anchor members 142, 144 having a frame structure. The frame shape can be polygonal as shown in the figure or it can alternatively be a circular shape. Other frame shapes are also possible as, for example, will be described below with respect to FIGS. 22 to 24.

A recovery suture can be attached to opposite ends of the proximate anchor member 142 to collapse the anchors for delivery in a catheter 146 as shown in FIG. 18 or for retrieval or repositioning. The anchor members can be made from a metal, preferably Nitinol, or polymers. Alternatively, as shown in FIG. 19, an anchor member 148 can include both metal and polymer components.

Figure 20A:
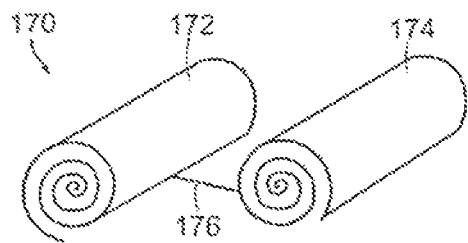
FIGS. 20A and 20B illustrate a PFO closure device having anchor members formed from a rolled material in accordance with one or more further embodiments of the invention in rolled and unrolled positions, respectively.

In accordance with one or more further embodiments of the invention, the distal and proximal anchors can be formed of a flat sheet-like member rolled to form a cylindrical shape as shown, for example, in the device 170 of FIG. 20A. The anchors 172, 174 can unroll to form sheet-like members when deployed, as shown generally in FIG. 20B. The sheet-like member can be made of a material having shape memory properties such as, for example, shape memory polymeric materials. Alternately, the sheet-like member can include metal struts made of shape memory metals such as, for example, Nitinol or Nitinol alloys. The shape memory materials allow the device to be delivered in a delivery sheath or catheter with the anchors in the rolled configuration of FIG. 20A. The anchors attain the sheet-like geometry of FIG. 20B once deployed due to their shape memory properties. The anchor members 172, 174 can be connected to each other with a connecting member 176, which can, for example, be a suture similar to that used in the FIG. 2 device.

Figure 20B:
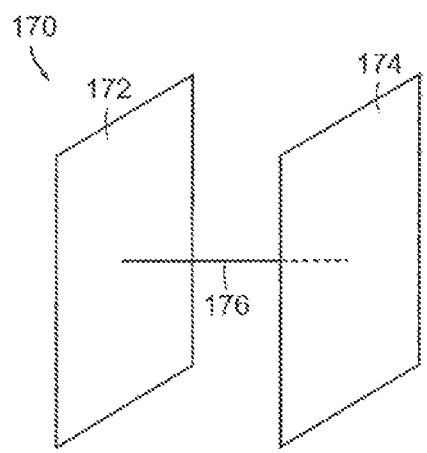
Figure 21A:
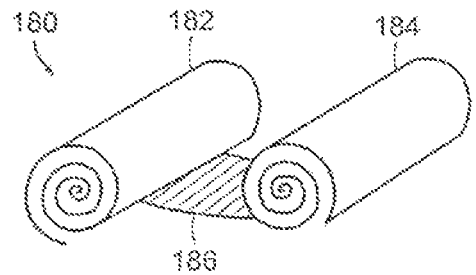
FIGS. 21A and 21B illustrate an alternate PFO closure device having anchor members formed from a rolled material in accordance with one or more further embodiments of the invention in rolled and unrolled positions, respectively.
Figure 21B:
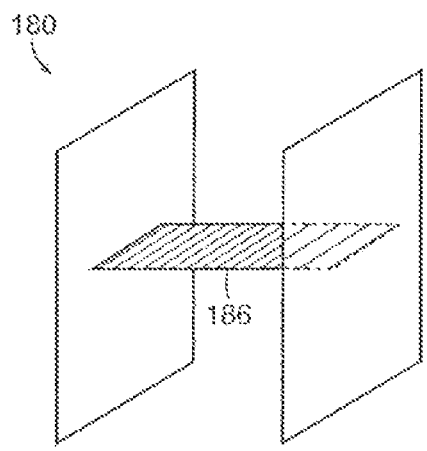

FIGS. 21A and 21B illustrate a closure device 180 having rolled anchor members 182, 184, which are similar to the anchor members 172, 174 of the device of FIGS. 20A and 20B. The anchors 182, 184 are connected to each other by a connecting member or joint 186, which can be a sheet of flexible material similar to the connecting members previously described with respect to FIGS. 6 and 7.

Figure 22A:
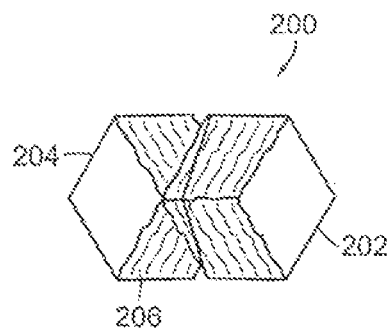
FIG. 22A illustrates a closure device having frame anchor members and a generally "X" shaped joint member in accordance with one or more further embodiments of the invention.
Figure 22B:
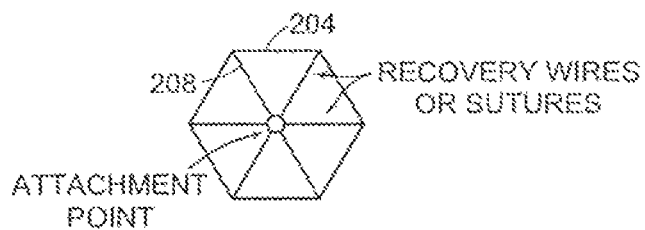
FIG. 22B illustrates the proximal anchor member of the FIG. 22A device.
Figure 22C:
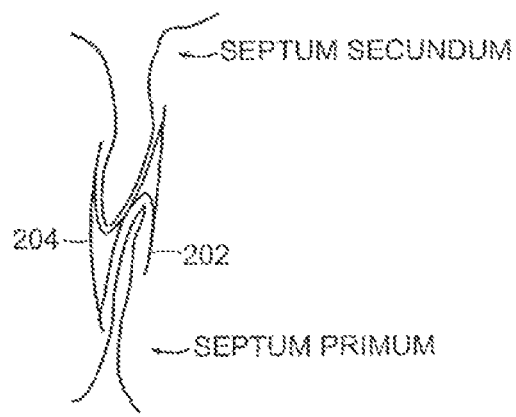
FIG. 22C illustrates the FIG. 22A device in a deployed state.

FIG. 22A illustrates a closure device 200 in accordance with one or more further embodiments of the invention. The device 200 includes distal and proximal anchor members 202, 204, each of which has a polygonal or circular frame structure. The anchor members are connected by a connecting member 206, which can be made from a flexible material similar to that previously described in connection with FIGS. 6 and 7. The connecting member 206 can be made of two sheets of flexible material connected at their centers, generally forming an "X" shape in the side view of the device. As shown in FIG. 22B, the proximal anchor member 204 can include one or more recovery wires or sutures attached to the frame structure for use in device deployment of recovery. FIG. 22C illustrates the device 200 as deployed.

Figure 23:
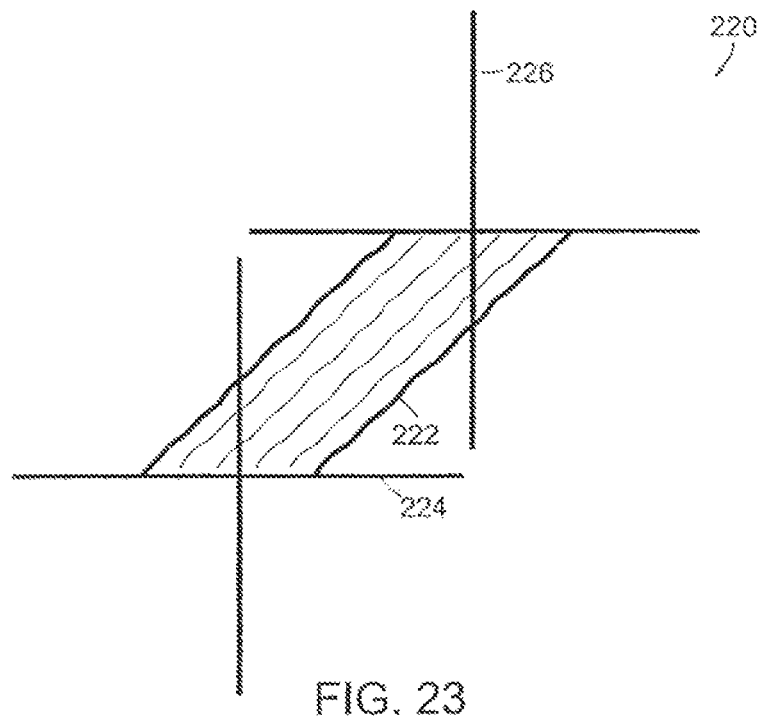
FIG. 23 illustrates a closure device having frame anchor members having a generally "+" shaped frame structure in accordance with one or more further embodiments of the invention.
Figure 24:
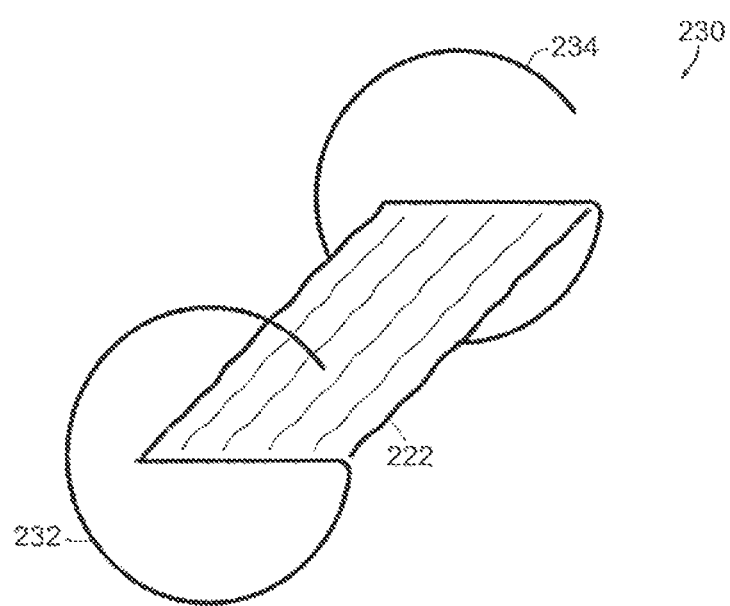
FIG. 24 illustrates a closure device having frame anchor members having a generally "G" shaped frame structure in accordance with one or more further embodiments of the invention.

FIGS. 23 and 24 illustrate closure devices 220, 230, respectively, in accordance with further embodiments of the invention. Each device 220, 230 includes distal and proximal anchor members having a frame structure. The anchor members are connected by a flexible joint 222, which can be made from a flexible material similar to that previously described in connection with FIGS. 6 and 7. The FIG. 23 device 220 includes distal and proximal anchor members 224, 226 generally having a "+" shape. The FIG. 24 device 230 includes distal and proximal anchor members 232, 234 generally having a "G" shape.

Figure 25:
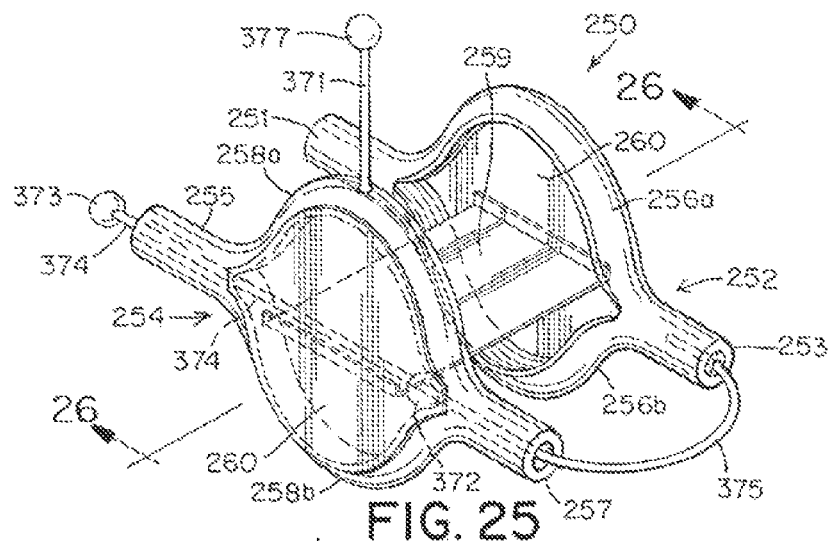
FIG. 25 is a perspective view of a two-dimensional closure device with anchor members having an elongate oval configuration in accordance with one or more further embodiments of the invention.
Figure 26:
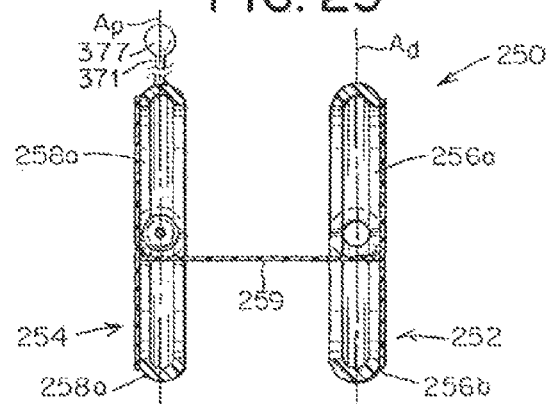
FIG. 26 is a cross-sectional end view taken along line 26-26 of the two-dimensional closure device of FIG. 25.
Figure 27:
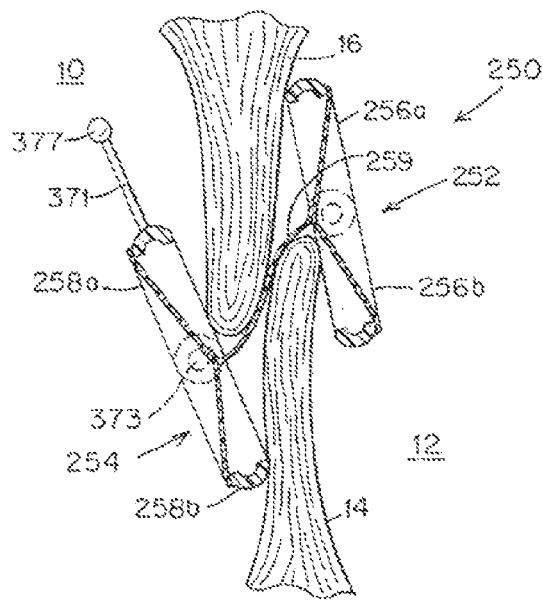
FIG. 27 is a schematic view of the two-dimensional closure device of FIG. 25 deployed at a delivery site in vivo.

In still further embodiments of the closure device 250 according to the present invention, the distal and/or proximal anchor members 252 and 254, respectively, may be formed, of cylindrical structures, split along the central portion of their length to provide elongate ovals (i.e., an "open-mouthed" configuration) as shown in FIGS. 25-27. In this elongate oval configuration, arcs 256 and 258 are joined by ends 251, 253 and 255, 257, respectively (FIG. 25). This configuration increases the size and surface area of the anchor member, thereby improving the dislodgement resistance of the closure device 250. As used herein, "dislodgement resistance" refers to the ability of a closure device to resist the tendency of the force applied by the unequal pressures between the right atrium 10 and the left atrium 12 (i.e. the "dislodging force") to separate the closure device from the septal tissue. Generally, a high dislodgement resistance is desirable.

Figure 28:
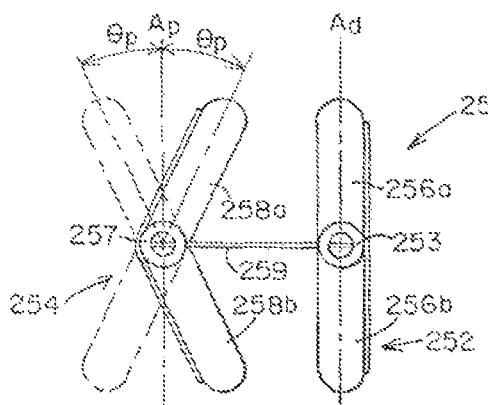
FIG. 28 is a schematic end view of a three-dimensional closure device with anchor members having an elongate oval configuration in accordance with one or more further embodiments of the invention.
Figure 29:
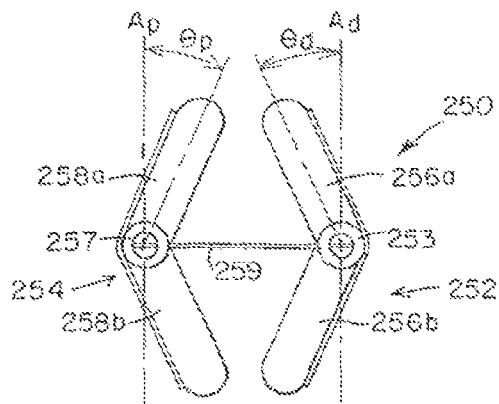
FIG. 29 is a schematic end view of a three-dimensional closure device with anchor members having an elongate oval configuration in accordance with one or more further embodiments of the invention.
Figure 30:
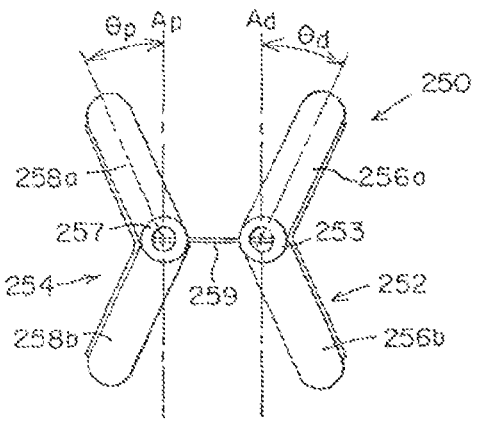
FIG. 30 is a schematic end view of a three-dimensional closure device with anchor members having an elongate oval configuration in accordance with one or more further embodiments of the invention.
Figure 31:
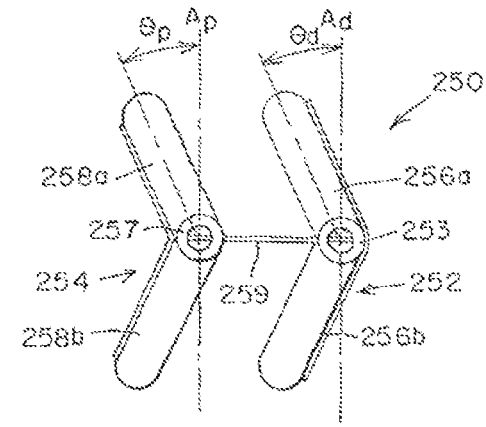
FIG. 31 is a schematic end view of a three-dimensional closure device with anchor members having an elongate oval configuration in accordance with one or more further embodiments of the invention.

Distal and/or proximal anchor members 252 and 254 having this elongate oval configuration may be either two-dimensional (FIGS. 25 to 27) or three-dimensional (FIGS. 28 to 32). As shown in FIG. 28, in the three-dimensional configuration, the arcs 258a and 258b of proximal anchor member 254 are predisposed to bend at an angle θ from the plane A of the two-dimensional proximal anchor member 254. Arcs 258a and 258b may bend at an angle θ either toward or away from center joint 259 (FIGS. 29 and 30, respectively). In particular embodiments, both distal anchor 252 and proximal anchor 254 are three-dimensional. In such embodiments, arcs 256a and 256b of distal anchor member 252 and arcs 258a and 258b of proximal anchor member 254 may bend at the same angle θ or at different angles $θ_{distal}$ and $θ_{proximal}$, respectively. Further, arcs 256a, 256b and 258a, 258b may bend toward center joint 259 (FIG. 29), away from center joint 259 (FIG. 30), or in opposite directions (i.e., one toward center joint 259 and one away from center joint 259, as shown in FIG. 31). As shown in FIGS. 28 to 32, arcs 256a, 256b and 258a, 258b include a straight bend; however, arcs 256a, 256b and 258a, 258b may also include a curved bend such that they are concave or convex. One skilled in the art will further recognize that, in a three-dimensional configuration, ends 251, 253 and 255, 257 may also be bent as described above for arcs 256a, 256b and 258a, 258b.

Figure 32:
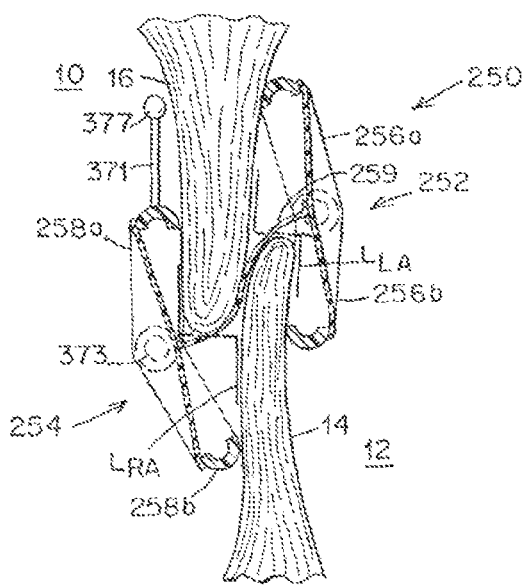
FIG. 32 is a schematic view of the three-dimensional closure device of FIG. 29 deployed at a delivery site in vivo.

In some clinical applications, a three-dimensional configuration of distal anchor member 252 and/or proximal anchor member 254 may be particularly advantageous. For example, septum primum 14 and septum secundum 16 are typically of disparate thickness, as shown in FIG. 32. Consequently, the septal tissue in the right atrium 10 is characterized by a step-like surface (indicated by line $L_{RA}$). The septal tissue in the left atrium 12 may also be characterized by a similar step-like surface (indicated by line $L_{LA}$). Insertion of a closure device including a two-dimensional anchor into a PFO surrounded by such step-like septal tissue often results in undesirable seating of that anchor member against the septal tissue, in that at least one arc of each anchor member does not contact the septal tissue, as shown in FIG. 27. However, the angled arcs of a three-dimensional anchor member may more closely approximate the step-like surface of the septal tissue, as shown in FIG. 32. Thus, in certain clinical applications, the use of a closure device including a three-dimensional distal anchor member 252 and/or proximal anchor member 254 may provide improved seating of the device 250 against the septal tissue and, correspondingly, a reduced profile of the device 250 and more effective closure of the PFO. As used herein, "profile" refers to the degree to which closure device 250 extends away from the septal tissue (i.e., septum primum 14 and septum secundum 16) and is exposed in the atria. A device having a "low profile" is closely seated against the septal tissue and extends only slightly, if at all, into the atria. A device having a "high profile" extends away from the septal tissue and into the atria. Generally, a device having a low profile is desirable because it is less thrombogenic in vivo. One skilled in the art will be capable of determining those clinical applications in which the use of three-dimensional anchor members is appropriate.

Either or both of distal anchor member 252 and proximal anchor member 254 having the above-described elongate oval configuration may include a tissue scaffold 260 extending between their two arcs 256a, 256b and 258a, 258b, respectively, as shown in FIG. 25. The inclusion of tissue scaffold(s) 260 augments the area of septal tissue covered by the anchor members 252 and/or 254. Consequently, device 250 provides improved closure of the PFO. Moreover, tissue scaffold 260 promotes encapsulation and endothelialization of the septal tissue, thereby further encouraging anatomical closure of the PFO. The tissue scaffold 260 may be formed of any flexible, biocompatible material capable of promoting tissue growth, including but not limited to, polyester fabrics, Teflon-based materials, ePTFE, polyurethanes, metallic materials, polyvinyl alcohol (PVA), extracellular matrix (ECM) or other bioengineered material, synthetic bioabsorbable polymeric scaffolds, other natural materials (e.g., collagen), or combinations of the foregoing materials. For example, the tissue scaffold 260 may be formed of a thin metallic film or foil, e.g., a nitinol film or foil, as described in United States Patent Application No. 2003/0059640 (the entirety of which is incorporated herein by reference).

Figure 33:
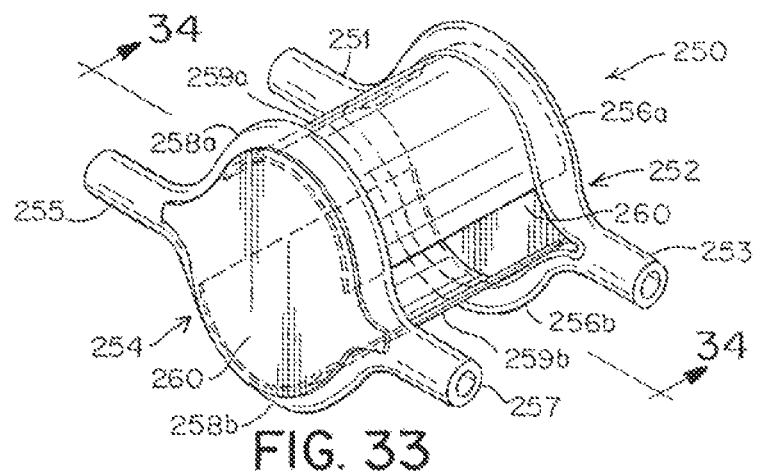
FIG. 33 is a perspective view of a two-dimensional closure device in accordance with one or more further embodiments of the invention.
Figure 48A:
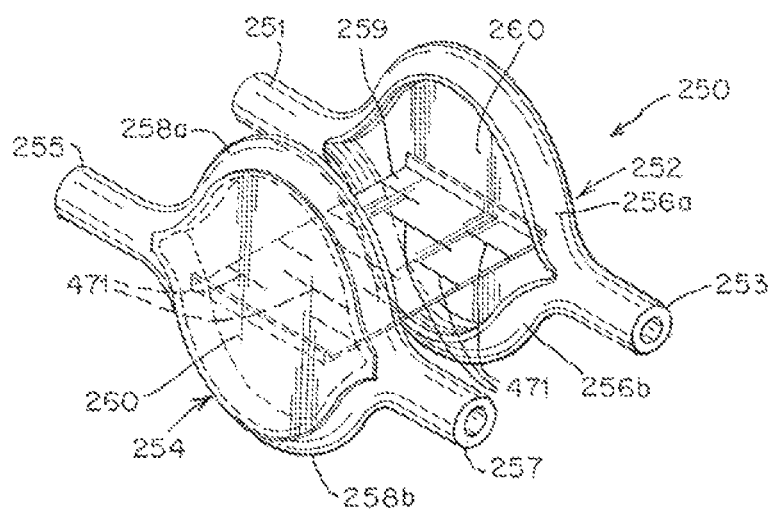
FIGS. 48A and 48B are perspective views of a two-dimensional closure device with anchor members having an elongate oval configuration in accordance with one or more further embodiments of the invention.
Figure 48B:
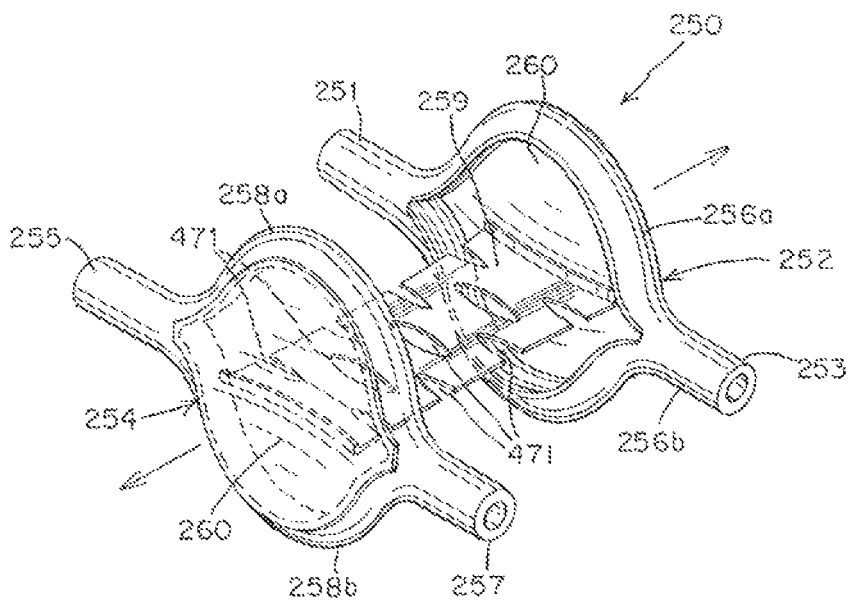

Distal anchor member 252 and proximal anchor member 254 may be connected by a flexible center joint 259 (FIG. 25). As previously described, in at least some embodiments, center joint 259 includes a stretchable elastomeric material. In at least some embodiments, center joint 259 includes a thrombogenic or inflammatory material, such as polyester, biological tissue, bioresorbable polymer, small diameter springs, e.g., nitinol springs, spongy polymeric material, or combinations of the foregoing materials. In at least some embodiments, center joint 259 is textured, porous, or in the form of a single- or double-sided hook material, such as Velcro. These types of surfaces produce inflammatory responses and, therefore, promote faster tissue ingrowth and defect closure. In particular embodiments and as shown in FIG. 25, center joint 259 is formed of a deformable or expandable film, such as those disclosed in United States Patent Application Nos. 2002/0165600 and 2002/0165576 (both of which are incorporated herein by reference). For example, center joint 259 may be formed of a shape memory film (e.g., nitinol film) or a polymeric film. Small openings 471, e.g., slits or holes, may be cut in the film such that, as the film expands upon deployment in vivo, the openings 471 also expand (FIGS. 48A and 48B). In this manner, the center joint 259 is rendered more flexible and capable of expanding significantly in length without placing excessive strain on the closure device (FIG. 48B). In some embodiments, the closure device 250 may include two flexible center joints 259a and 259b (FIG. 33).

Figure 35:
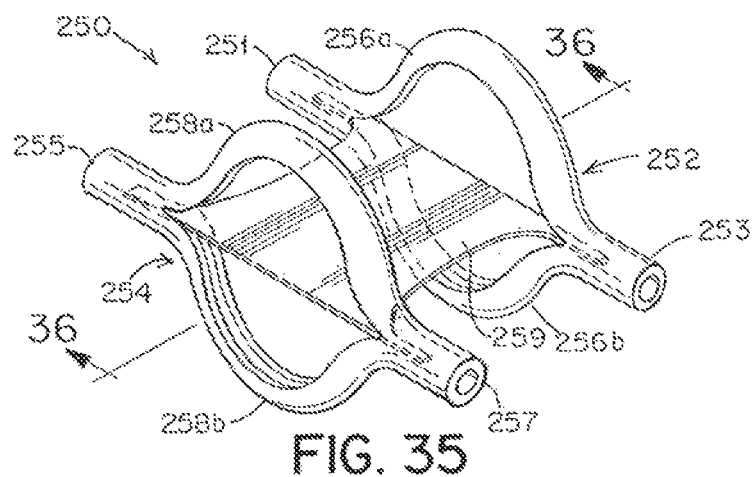
FIG. 35 is a perspective view of a two-dimensional closure device in accordance with one or more further embodiments of the invention.

Center joint 259 may be of various shapes and sizes depending upon the particular anatomy of the patient's septal tissue. For example, as shown in FIG. 25, center joint 259 may be generally rectangular. In other embodiments, and as shown in FIG. 35, center joint 259 may be shaped generally as an "X" or hourglass when in its relaxed configuration. Removing material from the sides of center joint 259 to form an hourglass shape increases its flexibility in vivo. The amount of material removed from the sides of a rectangular center joint 259 to form an hourglass shape will vary depending upon the particular application. According to some embodiments, between one-third and two-thirds of a rectangular center joint 259 will be removed to form the corresponding hourglass center joint 259. In particular embodiments, approximately one-half of a rectangular center joint 259 will be removed to form the corresponding hourglass center joint 259. In determining the precise amount of material to remove from the sides of a rectangular center joint 259 to form an hourglass center joint 259, a sufficient portion of center joint 259 must be retained to promote the healing response of the septal tissue that it contacts in vivo. One skilled in the art will be able to determine the precise amount of material that may be removed from a rectangular center joint 259 to form an hourglass center joint 259 suitable to the patient's septal anatomy while sufficiently maintaining the ability of center joint 259 to promote the healing of the septal tissue.

Figure 34:
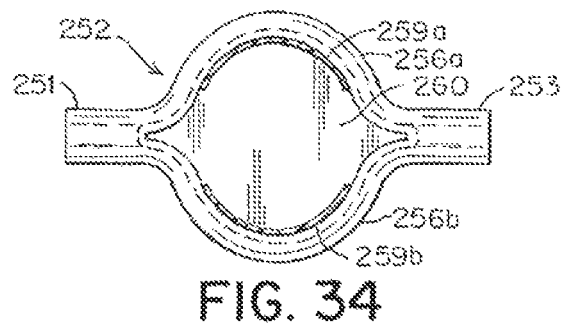
FIG. 34 is a cross-sectional view taken along line 34-34 of the two-dimensional closure device of FIG. 33.
Figure 36:
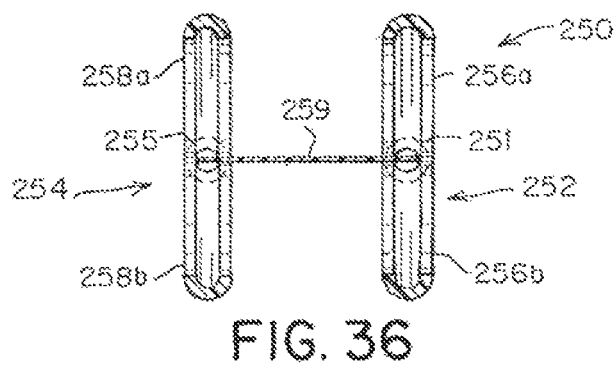
FIG. 36 is a cross-sectional end view taken along line 36-36 of the two-dimensional closure device of FIG. 35.
Figure 49A:
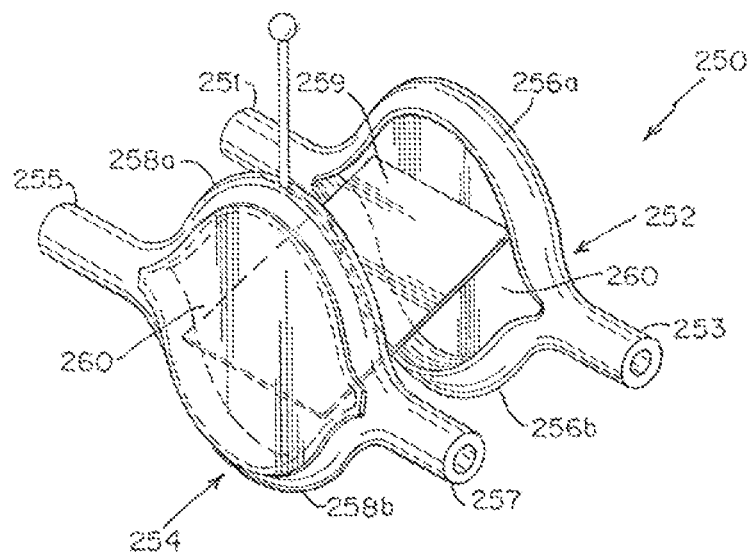
FIG. 49A is a perspective view of a two-dimensional closure device with anchor members having and elongate oval configuration in accordance with one or more further embodiments of the invention.
Figure 49B:
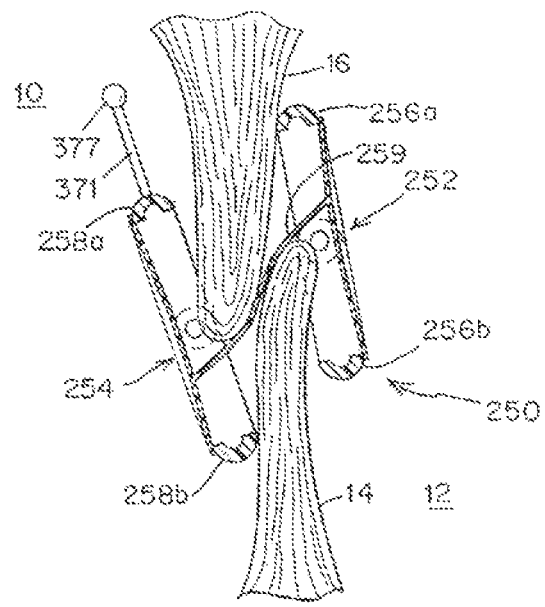
FIG. 49B is a schematic view of the two-dimensional closure device of FIG. 48 A deployed at a delivery site in vivo.

Center joint 259 may be connected to distal and proximal anchor members 252 and 254, respectively (FIGS. 35 and 36), or, if present, to tissue scaffolds 260 (FIG. 25). Center joint 259 may connect to tissue scaffolds 260 at their centers (FIG. 25), at a location on their peripheries (FIGS. 33 and 34), or somewhere in between (FIG. 48A). In particular embodiments, center joint 259 is connected at a location between the center and a periphery of tissue scaffold 260 on distal anchor member 252 and at a location between the center and opposite periphery of tissue scaffold 260 on proximal anchor member 254 (FIG. 49A) so as to more closely approximate the angled, tunnel-like anatomy of the PFO and reduce the profile of closure device 250 in vivo (FIG. 49B). For example, as shown in FIGS. 49A and 49B, center joint 259 may be connected to the tissue scaffold 260 of distal anchor member 252 at a location between the center of the tissue scaffold 260 and the arc 256a and connected to the tissue scaffold 260 of proximal anchor member 254 at a location between the center of tissue scaffold 260 and the arc 258b.

A closure device including a distal anchor member 252 and/or proximal anchor member 254 having an elongate oval configuration may be deployed or retrieved if arcs 256a, 256b and/or 258a, 258b, respectively, are collapsed to reduce the profile of closure device 250 such that it may be drawn into and contained within a delivery or retrieval catheter 370 (FIGS. 37-46). According to one embodiment and as shown in FIG. 25, closure device 250 may include a delivery string 371. As shown in FIG. 25, delivery string 371 is permanently attached to arc 258a of proximal anchor member 254, although one of skill in the art will recognize that delivery string 371 may be attached anywhere on proximal anchor member 254. Delivery string 371 may be attached in any suitable manner, for example, through a drilled hole, via glue, etc. Delivery string 371 is short (i.e., several millimeters) and as least thrombogenic as possible. As used herein, "string" includes various materials, which may be stiff or flexible. Delivery string 371 terminates in a ball 377 at its free end. Closure device 250 further includes a recovery ball 373 attached to recovery string 374, which is threaded through ends 255 and 257 of proximal anchor member 254 and subsequently attached to end 253 of distal anchor member 252. Slack 375 exists in recovery string 374 between end 253 of distal anchor member 252 and end 257 of proximal anchor member 254. Closure device 250 still further includes a ball 372 attached to recovery string 374 and contained between ends 255 and 257 of proximal anchor member 254. Ends 255 and 257 of proximal anchor member 254 may have an inner diameter greater than that of ball 372 but are tapered such that the terminal segment of ends 255 and 257 have a diameter smaller than that of ball 372. Thus, the movement of ball 372 is constrained between ends 255 and 257 of proximal anchor member 254.

Figure 37:
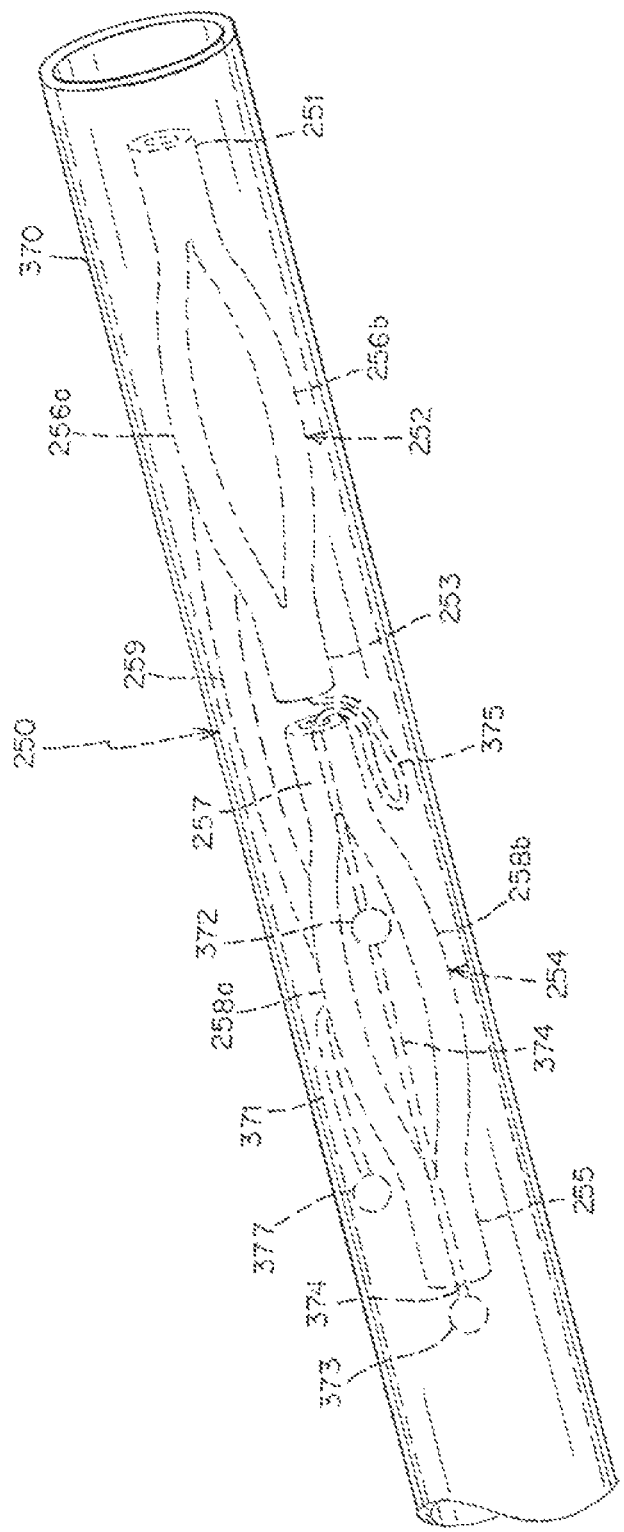
FIG. 37 is a schematic perspective view of the two-dimensional closure device of FIGS. 25 and 26 in a collapsed state and inserted into a catheter.

Prior to deployment in vivo, device 250 must be placed within delivery catheter 370 (FIG. 37). Device 250 may be loaded into catheter 370 in any manner such that slack 375 is maintained in recovery string 374 between distal anchor member 252 and proximal anchor member 254, as shown in FIG. 37. For example, device 250 may be manually loaded into catheter 370. One skilled in the art will be capable of identifying suitable methods for loading device 250 into catheter 370.

Figure 47:
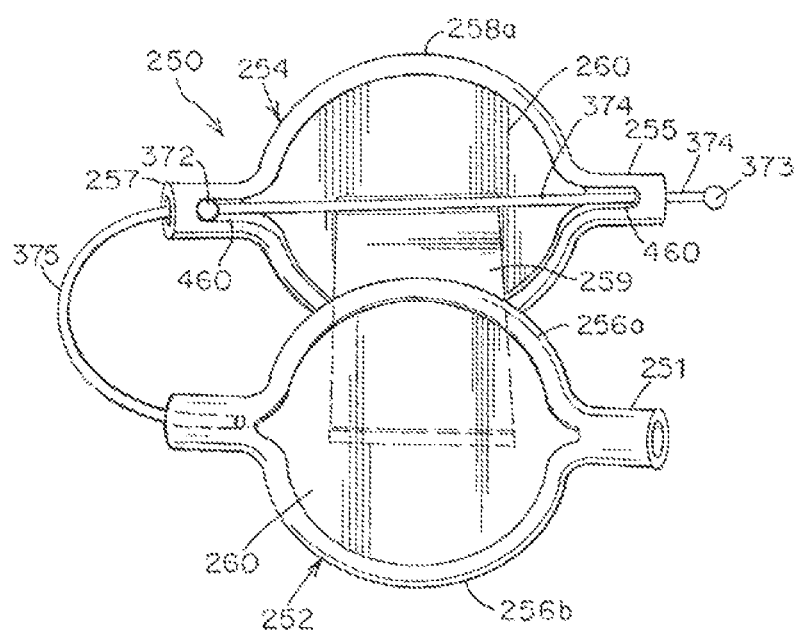
FIG. 47 is a perspective view of a two-dimensional closure device in accordance with one or more further embodiments of the invention.

One of skill in the art will, of course, recognize that the maximum amount of slack 375 in the recovery string 374 is dependent upon the distance ball 372 may travel between ends 255 and 257 of proximal anchor member 254. Slack 375 increases as ball 372 travels closer toward the terminus of end 257. Thus, the amount of slack 375 may be adjusted by altering the tapering of the internal diameter of ends 255 and 257. Additionally, the slit 460 splitting ends 255 and 257 of proximal anchor member 254 into arcs 258a and 258b may be extended toward the termini of ends 255 and 257 so as to maximize the distance ball 372 may travel within proximal anchor member 254 and, correspondingly, the slack 375 (FIG. 47).

Figure 38:
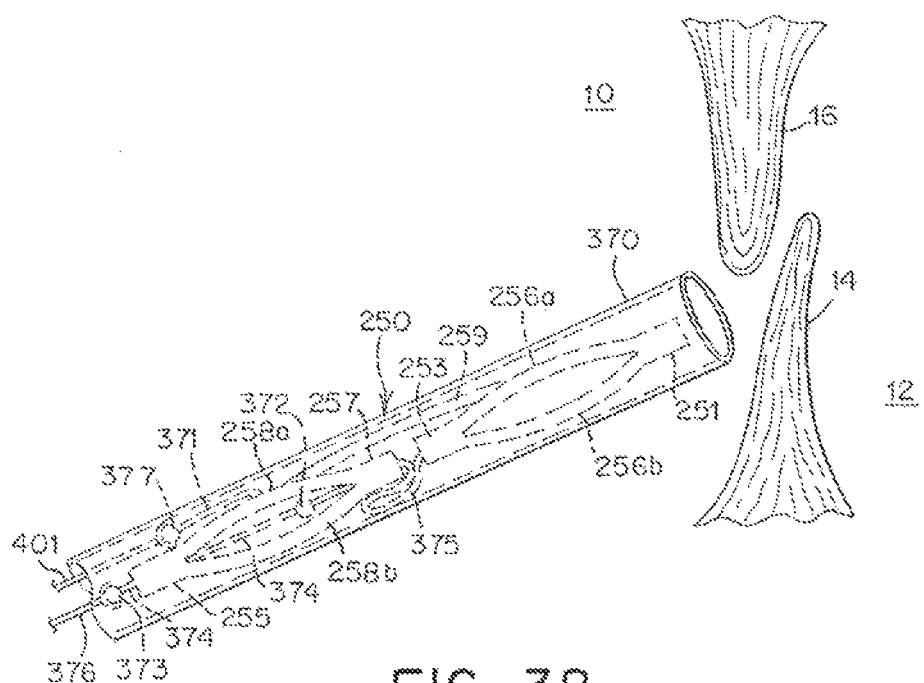
FIGS. 38 to 41 are schematic views of a method for delivering a closure device to an intended delivery site in vivo according to one or more further embodiments of the invention.
Figure 39:
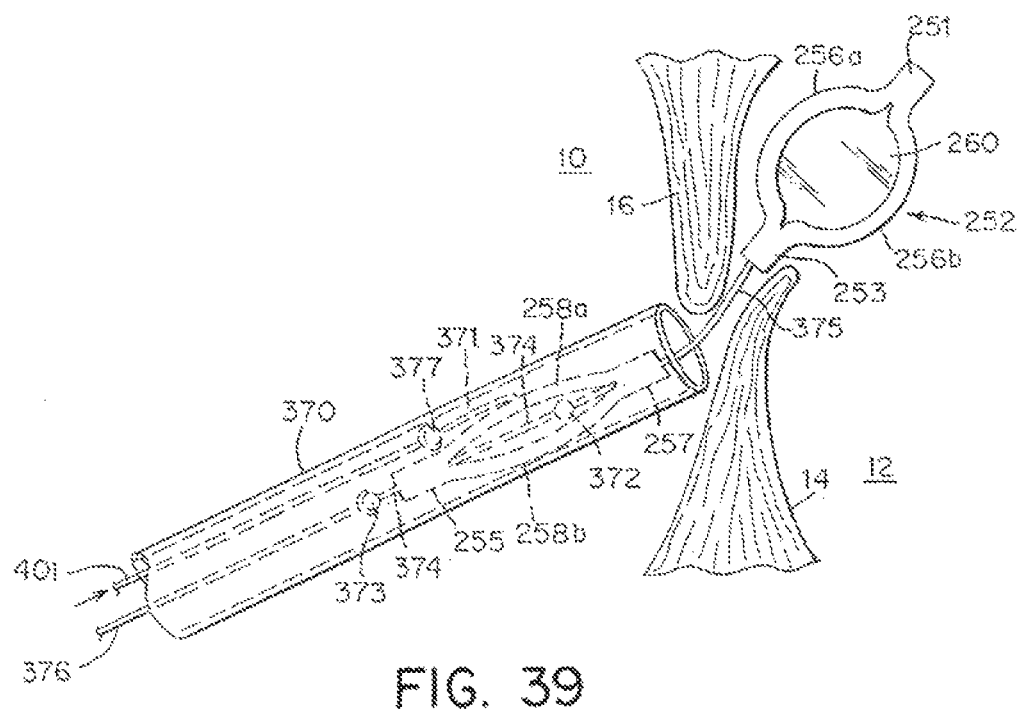

Device 250 may be delivered to its intended delivery site in vivo by various methods, only one of which will be described herein. As shown in FIG. 38, the clinician holds both recovery ball 373 and delivery ball 377 by suitable devices, e.g., grips 376 and 401. As used herein, the terms "ball" and "grips" are used to generically describe the delivery mechanism. One skilled in the art will recognize that the precise structure of the delivery mechanism components may vary. Grips 376 and 401 permit the clinician to apply tension or compression to delivery string 371 or recovery string 374 as desired to properly manipulate device 250. Generally, during delivery of device 250 by the method described herein, tension will be applied only to delivery string 371; recovery string 374 will be held in a relaxed configuration such that slack 375 is maintained. Once the clinician is properly holding both recovery ball 373 and delivery ball 377, catheter 370 is delivered through the patient's vasculature to the right atrium 10 of the heart (FIG. 38). Then, as shown in FIG. 39, catheter 370 is inserted between septum primum 14 and septum secundum 16 into the left atrium 12. Distal anchor member 252 is ejected into the left atrium 12 by pushing on grips 401, and arcs 256a and 256b reassume their elongate oval configuration (FIG. 39). Catheter 370 is withdrawn between septum primum 14 and septum secundum 16 and into the right atrium 10, such that proximal anchor member 254 is deployed into the right atrium 10 and slack 375 extends through the PFO (FIG. 40).

Figure 40:
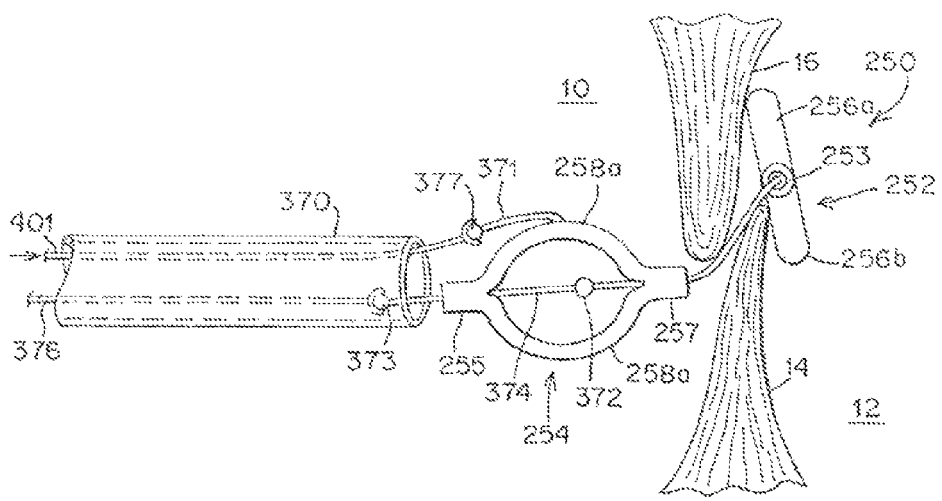
Figure 41:
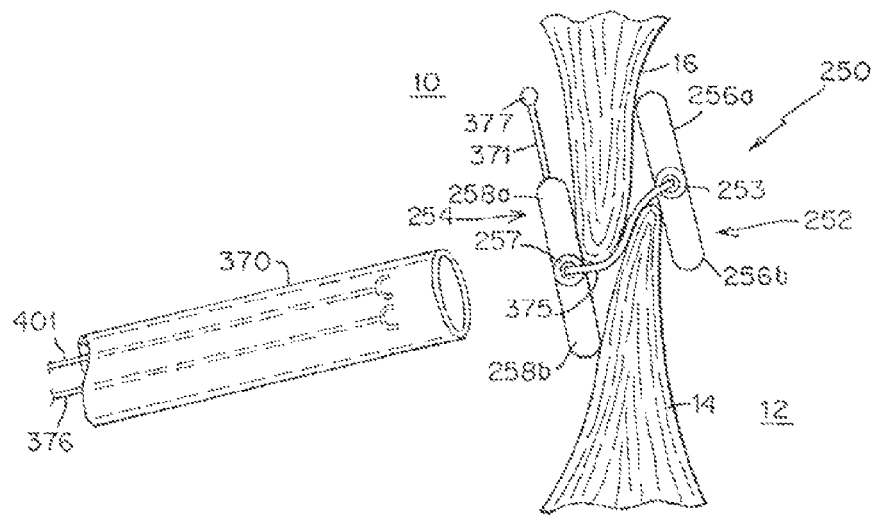

During this process, grips 401 are maintained on delivery ball 377, and the necessary tension is applied to delivery string 371 (FIG. 40). As shown in FIG. 40, arcs 258a and 258b reassume their elongate oval configuration upon deployment of proximal anchor member 254 into the right atrium 10, and proximal anchor member 254 may be positioned as desired against the septal tissue using grips 401. Distal anchor member 252 and proximal anchor member 254 cooperate to apply a compressive force to septum primum 14 and septum secundum 16, thereby closing the PFO (FIG. 41). If deployment of closure device 250 is satisfactory to the clinician, grips 401 release delivery ball 377, grips 376 release recovery ball 373 (FIG. 41), and catheter 370 is withdrawn from the right atrium 10 and further withdrawn through the patient's vasculature.

Figure 42:
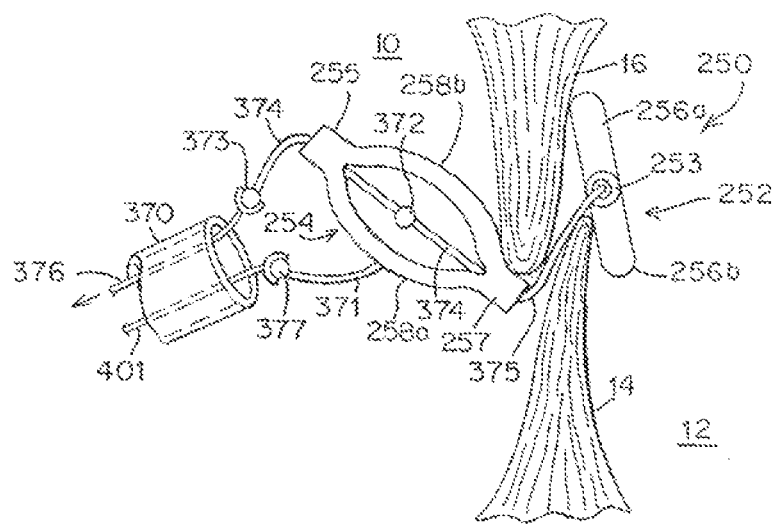
FIG. 42 is a schematic view of a method for repositioning a closure device at a delivery site in vivo according to one or more further embodiments of the invention.
Figure 43:
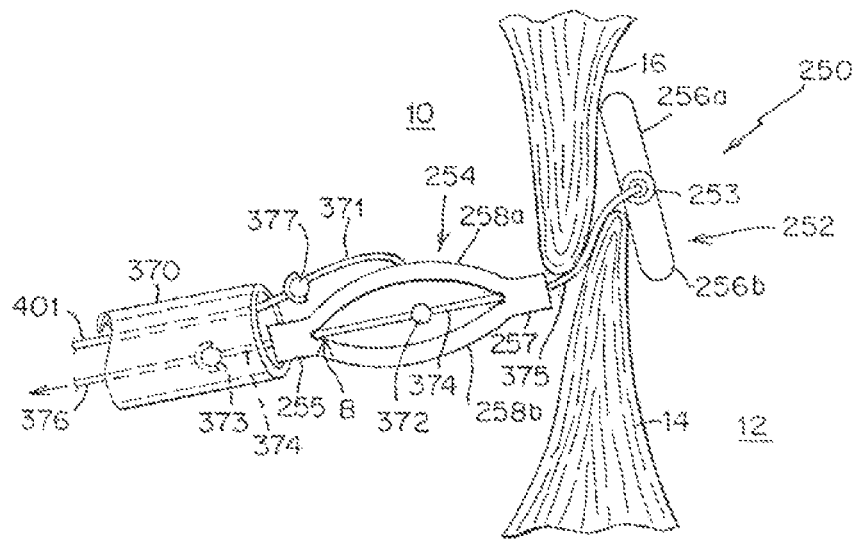
FIGS. 43 to 46 are schematic views of a method for retrieving a closure device from a delivery site in vivo according to one or more further embodiments of the invention.
Figure 44:
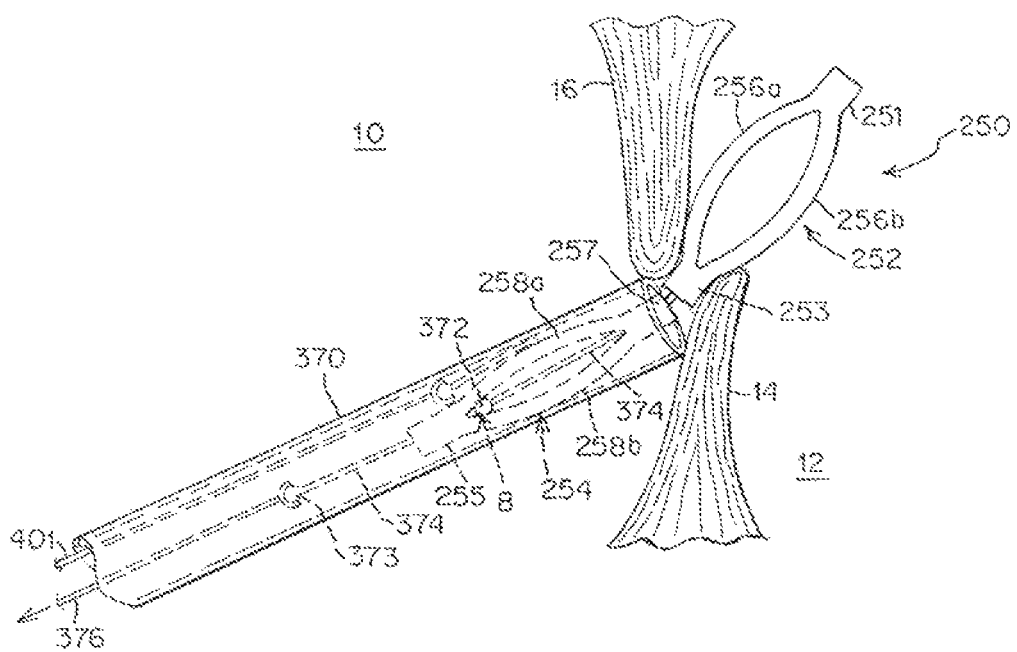
Figure 45:
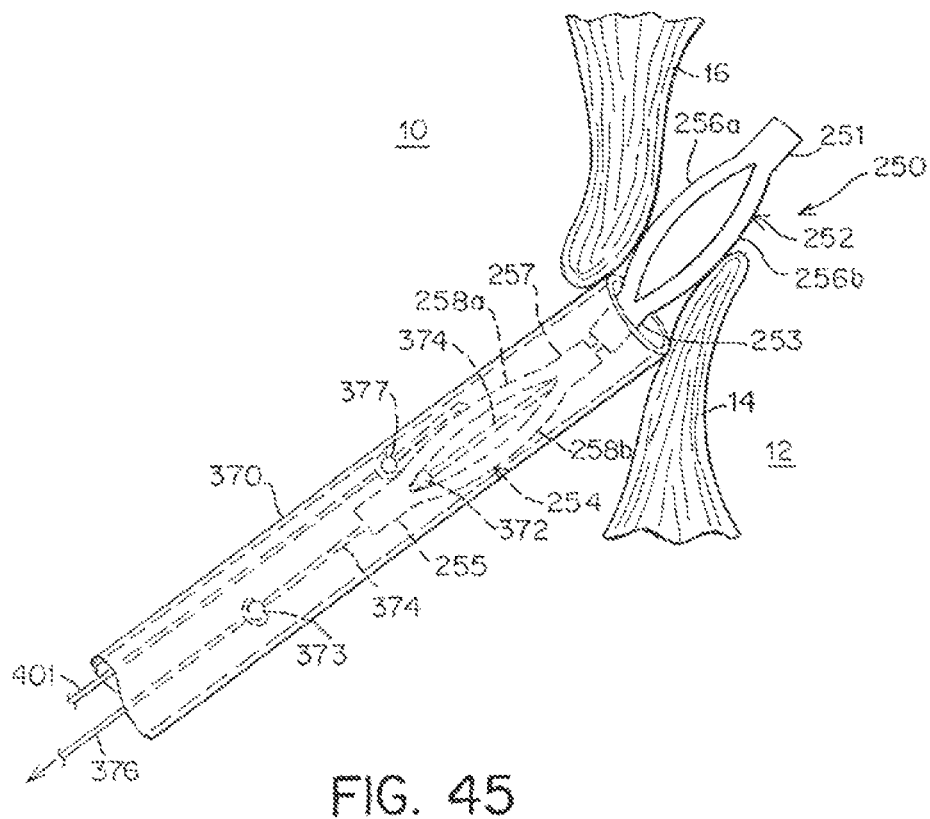
Figure 46:
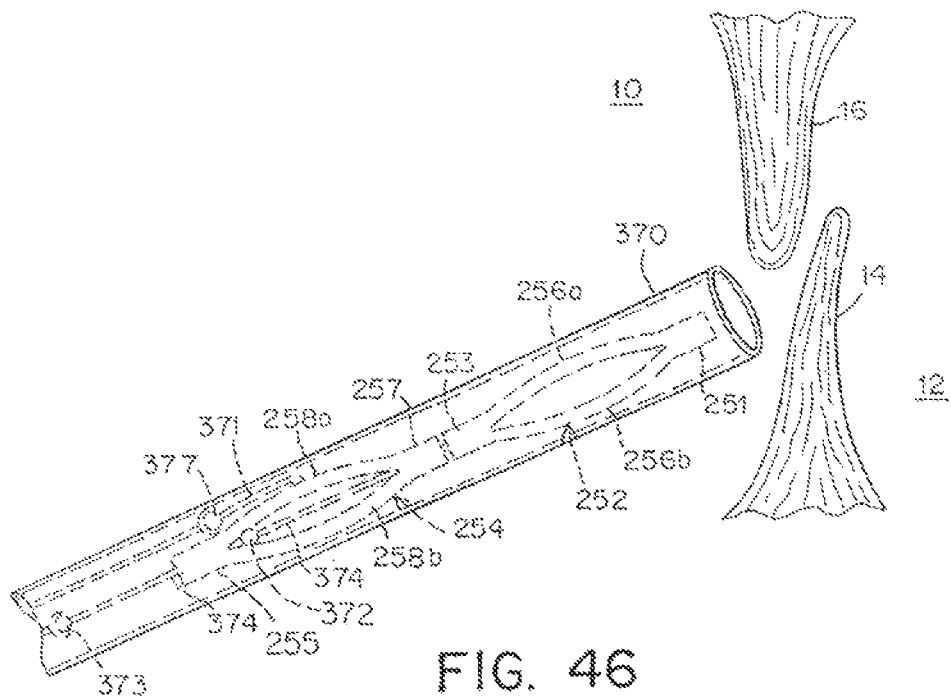

However, if, following deployment, the clinician is not satisfied with the position of device 250, grips 376 and grips 401 may be maintained on balls 373 and 377, respectively, so that the device 250 may be repositioned and/or retrieved. Device 250 may be repositioned by further manipulating the tension applied to delivery string 371 by grips 401 (FIG. 42). To retrieve closure device 250, catheter 370 is positioned against end 255 (FIG. 43). Recovery ball 373 is pulled into the catheter 370, such that ball 372 moves to point B of end 255 and arcs 258a and 258b of proximal anchor member 254 are collapsed and withdrawn into catheter 360 (FIG. 44). Upon nearing complete retrieval of proximal anchor member 254, slack 375 in string 374 is eliminated, or nearly so, and end 257 of proximal anchor member 254 and end 253 of distal anchor member 252 are touching, or nearly touching, such that proximal anchor member 254 and distal anchor member 252 are aligned in a longitudinal, end-to-end manner (FIG. 44). Grips 376 continue to apply tension to recovery string 374, pulling recovery ball 373 toward the proximal end of catheter 370, as shown in FIG. 45. Arcs 256a and 256b of distal anchor member 252 are collapsed, and distal anchor member 252 is withdrawn into catheter 370 (FIG. 45). Catheter 370 is then withdrawn through the PFO, and into the right atrium 10 (FIG. 46).

Figure 50:
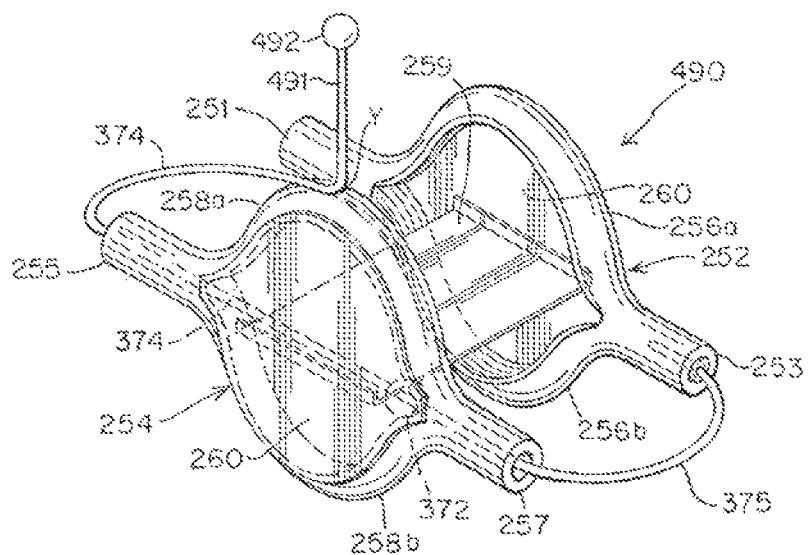
FIG. 50 is a perspective view of a two-dimensional closure device with anchor members having an elongate oval configuration in accordance with one or more further embodiments of the invention.
Figure 51:
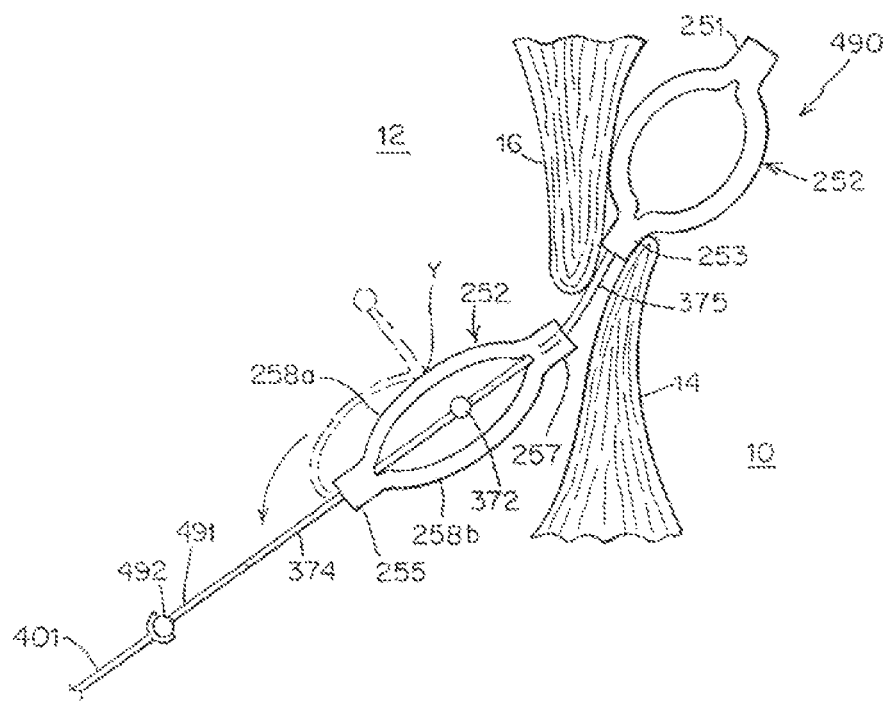
FIG. 51 is a schematic view of the two-dimensional closure device of FIG. 49 deployed at a delivery site in vivo.

The delivery and recovery system of device 250 may be modified in various ways, one of which is shown in the device 490 of FIGS. 50 and 51. String 374 may be extended from end 255 of proximal anchor member 254 toward arc 258a, be attached to arc 258 at a point Y, further extend from arc 258a to form delivery/recovery string 491, and terminate in delivery/recovery ball 492 (FIG. 50). The device 490 may be deployed as described above, except that only grips 401 would be necessary hold delivery/recovery ball 492 and manipulate the tension applied to delivery/recovery string 491 during delivery. To retrieve device 490, grips 401 apply sufficient tension to delivery/recovery string 491 to break its connection to arc 258a of proximal anchor member 254 at point Y (FIG. 50). By applying further tension to delivery/recovery string 374 by pulling delivery/recovery ball 492 towards the proximal end of the catheter 370, device 490 orients in a longitudinal manner and may be withdrawn into the catheter 370 as described previously.

The closure devices described herein can optionally be used along with suturing or stapling techniques where the anchors or flexible joints of the devices can be sewn or stapled to septum primum 14 and/or septum secundum 16 for better dislodgment resistance. Also, the flexible joint can, if desired, be covered with a biocompatible adhesive to adhere to the tissue or can be loaded with drugs or growth factors to promote healing. The adhesive and also certain drugs can also optionally be stored in any cavities in the anchor members 252 and/or 254 (e.g., in the cylindrical members of FIGS. 6 and 7) and released after deployment. Radiopaque markers can also be attached to the closure devices for better visualization during the implantation procedure. One skilled in the art will recognize that a variety of visualization techniques may be used, including fluoroscopy and magnetic resonance imaging (MRI).

The various closure devices described herein may further include a number of advantageous features. The closure devices preferably have an atraumatic shape to reduce trauma during deployment or removal. In addition, the devices can be self-orienting for ease of deployment. Furthermore, because of the flexible center joint, the devices generally conform to the anatomy instead of the anatomy conforming to the devices, which is especially useful in long tunnel defects. In addition, the devices can preferably be repositioned and/or removed during delivery. The devices also generally have a relatively low profile after deployment. The flexible center joint 259 of the devices can encourage faster tissue ingrowth and therefore, faster defect closure. Furthermore, there are generally no exposed thrombogenic components in the left 12 and right 10 atria. Still further, the devices may advantageously include bioresorbable components, which will disappear from the body over time.

One skilled in the art will recognize that the features of any embodiment described herein may be combined with those of any other embodiment described herein.

Other benefits of the devices described herein include the possible use of a relatively small diameter delivery sheath, use of a reduced amount, or no, metal mass in the device, ease of manufacturing, cost effectiveness, and overall design simplicity.

Having described preferred embodiments of the present invention, it should be apparent that various modifications may be made without departing from the spirit and scope of the invention, which is defined in the claims below.

What is claimed is:

1. A device for closing a defect in septal tissue, comprising:
 a first side adapted to be disposed on one side of the septal tissue and a second side adapted to be disposed on the opposite side of the septal tissue, said first and second sides connected by two flexible center joints extending from the first side to the second side,
 wherein each of said first and second sides includes an anchor member, and
 wherein the anchor member of at least one of said first and second sides comprises a generally cylindrical member having a central portion, wherein the central portion is split to form an elongate oval having a surface area adapted to seat against the septal tissue.

2. The device accordingly to claim 1, wherein the first anchor member includes a tissue scaffold attached to generally cylindrical member, wherein the center joint is further attached to the tissue scaffold such that the longitudinal axis of the generally cylindrical member extends generally transverse to the center joint when the device is deployed.

3. The device according to claim 2, wherein the tissue scaffold is bioresorbable.

* * * * *